United States Patent [19]
Prince

[11] Patent Number: 5,178,603
[45] Date of Patent: Jan. 12, 1993

[54] BLOOD EXTRACTION AND REINFUSION FLOW CONTROL SYSTEM AND METHOD

[75] Inventor: Paul R. Prince, San Juan Capistrano, Calif.

[73] Assignee: Baxter International, Inc., Deerfield, Ill.

[21] Appl. No.: 556,778

[22] Filed: Jul. 24, 1990

[51] Int. Cl.⁵ ............................................. A61M 1/03
[52] U.S. Cl. ........................................ 604/6; 604/4; 604/65
[58] Field of Search .................. 604/30, 31, 65-67, 604/4-6, 50; 128/DIG. 12, DIG. 13

[56] References Cited

U.S. PATENT DOCUMENTS

| | | | |
|---|---|---|---|
| 4,086,924 | 5/1978 | Latham, Jr. | 604/6 |
| 4,191,182 | 3/1980 | Popovich et al. | 128/214 |
| 4,285,464 | 8/1981 | Latham, Jr. | 233/26 |
| 4,468,219 | 8/1984 | George et al. | 604/66 |
| 4,605,503 | 8/1986 | Bilstad et al. | 210/651 |
| 4,648,866 | 3/1987 | Malbrancq et al. | 604/5 |
| 4,655,742 | 4/1987 | Vantard | 604/6 |
| 4,657,529 | 4/1987 | Prince et al. | 604/6 |
| 4,687,580 | 8/1987 | Malbrancq et al. | 210/651 |
| 4,904,234 | 2/1990 | Shimomura et al. | 604/5 |
| 4,954,128 | 9/1990 | Ford | 604/5 |
| 5,045,057 | 9/1991 | Van Driessche et al. | 604/50 |

FOREIGN PATENT DOCUMENTS

| | | |
|---|---|---|
| 0052004 | 11/1981 | European Pat. Off. . |
| 0085016 | 1/1983 | European Pat. Off. . |
| 0122604 | 4/1984 | European Pat. Off. . |
| 0042939 | 4/1986 | European Pat. Off. . |
| 0303765 | 2/1989 | European Pat. Off. . |
| WO83/02059 | 6/1983 | PCT Int'l Appl. . |
| WO84/02473 | 7/1984 | PCT Int'l Appl. . |
| 2135598A | 9/1989 | United Kingdom . |
| WO86/00231 | 1/1986 | World Int. Prop. O. . |
| WO86/01416 | 3/1986 | World Int. Prop. O. . |
| WO86/0285-8E | 5/1986 | World Int. Prop. O. . |

OTHER PUBLICATIONS

"Non-Recursive Matched Filters Using Charge-Coupled Devices", pp. 244-247.

Primary Examiner—Stephen C. Pellegrino
Assistant Examiner—Ralph A. Lewis
Attorney, Agent, or Firm—Bruce M. Canter; June M. Bostich; Robert D. Buyan

[57] ABSTRACT

A method and system for adaptively controlled withdrawal/infusion of a fluid, such as blood, to or from a fluid source, such as a blood vessel. An adaptive flow rate limit is established and periodically adjusted during the course of withdrawal/infusion so as to maximize and optimize the withdrawal/infusion rate while, at the same time, providing for rapid corrective adjustments in flow rate responsive to early indications of flow disruption, such as occlusion or collapse of the blood vessel during blood withdrawal. The method and system of the invention is particularly applicable to automated apheresis systems.

51 Claims, 13 Drawing Sheets

BLOOD EXTRACTION AND REINFUSION FLOW CONTROL SYSTEM AND METHOD

BACKGROUND OF THE INVENTION

1. Field of the Invention

This invention relates to a living subject adaptive blood flow control system and more particularly to a plasmapheresis blood flow control system which optimizes blood flow by limiting and/or otherwise altering the blood flow rate in accordance with a flow control curve determined individually for each donor or patient subject from actual subject data. More particularly, this invention relates to an improved blood flow control system for controlling and optimizing the rate of blood withdrawal/reinfusion from a blood vessel, thereby mitigating the frequency and/or severity of occlusive interruptions (e.g. collapse of vein or collapse of tubing) in the course of blood withdrawal).

2. Discussion of the Prior Art

Blood collection systems and apheresis systems such as plasmapheresis, platelet pheresis, therapeutic plasma exchange or processing, etc. as well as other systems are known which require the extraction or reinfusion of bodily fluids from or to a living subject. The subject is typically a living human or animal subject but might also be a cadaver. In the case of a plasmapheresis system whole blood is extracted from the subject, plasma is separated from the whole blood, and an extraction product containing a higher concentration of blood cells than the whole blood is reinfused back to the subject while the separated plasma is retained and used for desired purposes. Frequently, a selected volume of saline solution or other fluids are infused into the subject to replace the volume of plasma separated from the whole blood.

To optimize utilization of processing equipment and support personnel and minimize inconvenience and discomfort to the subject, it is often desirable to remove or reinfuse bodily fluids as rapidly as possible. However, physiological restrictions on flow rates impose practical limitations on how fast pumping can proceed.

During extraction, if the pumping rate exceeds the flow capacity of a vein into which a phlebotomy needle or catheter is inserted, the intravenous pressure will drop below approximate atmospheric pressure and the vein sidewalls will collapse under atmospheric pressure. When such collapse of the vein occurs, the blood pump must be stopped or significantly slowed until the intravenous blood flow restores the intravenous pressure to a point greater than atmospheric pressure, thus refilling the collapsed portion of the vein.

Oftentimes, when the vein collapses about the needle, the end of the needle will become compressed against the sidewall of the vein. When this happens the needle will frequently become embedded within the vein sidewall or will be sealed to the vein wall by virtue of the negative pressure within the needle and tubing that can be developed following a sudden occlusion. The needle then remains occluded, even after the previously collapsed vein has been refilled with blood. It may then become necessary to remove and reposition the needle at the expense of considerable additional time delay.

Reinfusion presents a somewhat different flow rate problem from extraction. During reinfusion, if the pumping flow rate exceeds the vein flow capacity, the intravenous pressure increases until either the phlebotomy needle is forced out of the vein or the vein swells or even bursts or leaks into surrounding tissue. This creates an undesirable hematoma.

Predicting the optimal rate at which blood may be extracted from a blood vessel is difficult because intravascular flow rates and volumes vary considerably from subject to subject. Even for a given subject, the intravascular flow rate capacity can vary considerably over a given time period. When blood is being withdrawn from a peripheral vein, (e.g. a superficial vein of the antecubital fossa), moment to moment variations in blood flow through the peripheral vein may be observed due to changes in physiological variables and/or contraction/relaxation of the muscles surrounding the blood vessel. In an effort to maintain relative continuity of blood flow through the vein it is common practice to require the donor to engage in alternate contraction/relaxation of the muscles during the blood withdrawal process—usually by squeezing an object held with the hand adjacent the withdrawal site. If, however, the donor/subject is less than diligent in squeezing the object, or if the donor only squeezes the object for intermittent periods, such may result in extreme variations in blood flow within the peripheral vein during the blood withdrawal process.

Attempting to optimize the pump blood flow rate by sensing flow path pressure adjacent the needle is uncertain because the pressure drop across the needle varies substantially with flow rate, hematoit dependent blood viscosity and needle size parameters. It is therefore common to rely on a gravity driven flow rate far below the optimum or a pumping rate that is known to be well within the blood flow capacity of most subjects. This may be far below the optimum flow rate.

One arrangement in which a plasmapheresis system serves as a reservoir for receiving and returning bodily fluids is described in U.S. Pat. No. 4,086,924 to Latham, Jr. for "Plasmapheresis Apparatus". In this system extraction occurs under vein pressure and gravity. A multi-rate blood pump for the plasmapheresis system is accelerated or decelerated to match this flow rate. Reinfusion occurs at a predetermined rate with the blood pump set to a relatively low speed condition.

A more capable blood flow control system is disclosed in U.S. Pat. No. 4,657,529 to PRINCE, ET AL., which has been assigned to the common assignee herein. As with the present system, the system disclosed in the prior patent utilizes a programmed digital processor to regulate blood flow based on sensed fluid pressure in the flow path. The flow rate, i.e. pump speed, is regulated to achieve a maximum flow rate consistent with avoiding vein occlusions. Though this system provides a significant improvement over prior blood flow control systems, experience has indicated that still further improvements are useful in order to extend the operating range of the system to accommodate very low blood flow subjects and high blood flow subjects. Moreover, it is desirable to increase the rate at which the patented blood flow control system reaches the optimum rate for each subject while decreasing the number and likelihood of occlusions in the course of reaching that optimal rate. Additionally, it is desirable in some systems to employ two needles, one dedicated to extraction and one to reinfusion. It is desirable to calibrate each of these needles (which may be of different size) and to adjust the control system according to known variations in the viscosity of the fluid (e.g. whole blood, saline, blood cell concentrate) being withdrawn- /infused through the needles. In view of the high usage rate of blood flow control systems such as the patented system (estimated at approximately 300,000 procedures per month) such advantages in the range and speed of the blood flow control system of significant medical and commercial value including reducing anxiety associated with such procedures and increasing the number of procedures that each system complete during a normal operating day.

SUMMARY OF THE INVENTION

The present invention comprises a system for withdrawing and/or infusing fluid from the human body at adaptively controlled flow rates.

In accordance with a broad aspect of the invention, there is provided a method and system for withdrawing a fluid such as blood from a variable source such as a blood vessel. The system may comprise a fluid reservoir fluidly connected to a blood vessel by a first fluid flow path. A pump is provided for pumping blood from the blood vessel, through the first fluid flow path to the fluid reservoir. A pressure sensor is provided for sensing pressure within the first fluid flow path and a flow rate sensor is provided for sensing the flow rate within the first fluid flow path. A flow rate control system is provided to receive and process the sensed pressure and sensed flow rate and to provide flow rate control signals to the pump, in accordance with the sensed changes in the pressure and flow rate. The control system is generally programmed and adapted to carry out the steps of the method of the present invention, such as:

(a) receive and store a maximum flow rate limit setting;
(b) store a standard flow rate/pressure curve defining the flow rate versus pressure relationship of blood being withdrawn freely through the first flow path without restriction;
(c) calculate a control curve related to and below said standard flow rate/pressure curve;
(d) establish an initial adaptive flow rate limit no greater than said maximum flow rate limit;
(e) signal said pump to pump blood at said initial adaptive flow rate limit for a first timed pumping period;
(f) determine whether the pressure within the flow path has remained above the control curve throughout the immediately preceding pumping period and, if so, then increase the adaptive flow rate limit by a predetermined increment amount and, thereafter, signal the pump to pump blood at the then current adaptive flow rate limit for a subsequent timed pumping period;
(g) determine whether the pressure within the first flow path has fallen below the control curve during the immediately preceding pumping period and, if so, signal the pump to slow the flow rate of blood to a point where pressure within the first path is stabilized on said control curve and, thereafter, maintain pumping at such stabilized flow rate for a timed stabilization pumping period.

Additionally, after the timed stabilization period has been completed, the controller may be programmed to determine whether the stabilization point on said control curve lies more than a predetermined distance below the then current adaptive flow rate limit (e.g. within a "target flow rate zone" of less than approximately 2 to 20 ml/min. and preferably less than about 5 ml/min. below the existing adaptive flow rate limit). If the stabilization point is more than such predetermined distance below the then current adaptive flow rate limit, the controller will lower the adaptive flow rate limit by a predetermined decrement amount (e.g. 5 ml/min.). Thereafter, the system will carry out a timed pumping period at such decreased adaptive flow rate limit and will thereafter repeat steps (f) and (g) as set forth above, so as to cause the flow rate to be subsequently advanced if the detected preocclusive state was of a transient nonpersistent nature. Thereafter, the controller may be programmed to once again increase the adaptive flow rate limit and to thereafter signal the pump to pump blood at the new increased adaptive flow rate limit, repeating the above-described steps (f) and (g) in accordance with the sensed flow rate and pressure within the first flow path.

Still further in accordance with the invention, the control system (e.g. computer) may be further programmed to compute and monitor the rate of change of pressure (e.g. one or more derivative functions of pressure with respect to time ($dp/dt$ or $dp^2/dt^2$)) within the first flow path. The control system will then analyze the rate of change of pressure (e.g. the derivative function(s)) to determine when the pressure dynamics within the flow path are indicative of impending occlusion of the flow path or collapse of the blood vessel. The point or points at which such pressure dynamics are indicative of impending occlusion or collapse of the blood vessel may be defined empirically and/or on the basis of experimentally generated data. Also various mathematical signal conditioning processes (e.g. matched filters, correlation filters and/or analysis of the pressure signal by convolutions matched filter functions) may be utilized to combine pressure function(s) (e.g. p, $dp/dt$ and/or $dp^2/dt^2$) in a manner which will optimize the reliability and reproduceability with which impending occlusion and/or collapse of the blood vessel may be predicted while minimizing the susceptability of the system to erroneous or artifactual triggering due to electrical noise or other noise as may result from aberrant motion, or movement of the system or human subject or other causes. Such filters can be "matched" to the signal characteristics and "mismatched" to noise characteristics. Upon ascertaining when the pressure dynamics within the flow path are indicative of impending occlusion or vein collapse, the controller will then provide corrective signals to the pump(s) (e.g., signaling the pump to cease pumping blood) and will, thereafter, cause the pump flow rate to be decreased to a point where the pressure within the flow path will stabilize at or near the steady state (e.g. on the control curve) control curve. Also, the adaptive flow rate may be decremented to a lower point and, thereafter, steps (f) and (g) may be repeated to immediately rechallenge the system and the subject to support a higher blood withdrawal rate despite detection of the previous preocclusive event.

Still further in accordance with the invention, the adaptive flow control system may be additionally applied to infusion of fluids and/or reinfusion of blood constituents. Generally, the adaptive flow rate control method and system of the present invention is applied to infusion/reinfusion in the same manner that it is applied to blood withdrawal procedures as described above. In "single needle" procedures where fluid is alternately withdrawn and infused through a single flow path, an infusion/reinfusion control curve is established on the basis of the same data used to establish the withdrawal control curve (i.e. based on the previously generated standardized flow curve). However, because slight over pressurizations during fluid infusion/reinfusion are more acceptable than during withdrawal, and further because the viscosity of fluid being infused/reinfused typically differs from that of the blood which was previously withdrawn, the infusion/reinfusion control curve is adjusted upwardly or "translated" by a predetermined pressure adjustment factor (e.g. 48 mm. Hg.). Additionally, the slope of the infusion/reinfusion control curve may be adjusted by a slope adjustment factor to correct or compensate for known or expected differences in viscosity between the fluid being infused/reinfused and the whole blood or other fluid from which the control curve was originally generated. For example, in apheresis applications where whole blood is withdrawn and cell concentrate (blood cells plus a small amount of plasma) is reinfused, the slope of the reinfusion control curve may be multiplied by a slope correction factor of approximately $-2.0$. Such alteration in the slope of the reinfusion control curve slope is determined to substantially account for differences in the pressure/flow dynamics of cell concentrate as opposed to whole blood. The applicable slope correction factor may be estimated, measured, or calculated on the basis of data obtained by any presently or hereafter known methods for measuring hematocrit and/or fluid viscosity. In "two needle" procedures wherein fluid is withdrawn through a first flow path and fluid infused/reinfused through a second flow path, separate standard flow/pressure and control curves are established for infusion through the second flow path. Thereafter, the height of such control curve is then translated by a predetermined pressure adjustment factor and the slope of such translated control curve will be adjusted for the instant viscosity by applying a slope correction factor in the manner described above for single needle applications.

Further, in accordance with the invention, there is provided an individually adaptable bodily fluid flow control system for an apheresis system. The fluid control system controls fluid flow at an optimal rate for each different subject. The flow control system includes a pump disposed to pump blood or other bodily fluids through a flow path between a phlebotomy needle or other donor attachment and a reservoir such as a plasma separation system. The system further includes a pressure sensor disposed to sense fluid pressure in the flow path between the needle and the pump, a controller coupled to the pump flow rate in response to the sensed pressure and the actual pump operating speed, and a control panel coupled to convey operator commands to the controller.

The controller includes a programmed digital processor which operates for each new subject to determine zero flow vein pressure as well as sensed pressure at a test point flow rate which is selected to be within the substantially linear flow rate capacity of the subject. To increase the zero flow vein pressure and thereby the dynamic range of operating internal vein pressures, a pressure cuff disposed near the needle and downstream of the vein blood flow direction may be used. The test point data is extrapolated to higher flow rates and translated by an amount less than the zero flow vein pressure to form a flow rate control curve. The controller then commands the fluid pump to maintain the system at a desired maximum nominal flow rate subject to any limitations imposed by the flow rate control curve. By using actual test point data the flow rate control curve can be individually adapted to the hematocrit dependent viscosity, tubing dependent pump flow constant, and needle characteristics encountered in each instance of use. It can be adjusted thereafter, if desired, to account for changes made to the pressure cuff pressure setting.

The digital processor operates on discrete (e.g. 50 msec) computer cycles. Such computer cycles periodically update flow rate commands to the pump. During each computer cycle the processor (a) samples the sensed pressure, (b) provides atmospheric calibration therefor and, then, (c) provides lead-lag compensation to generate a compensated pressure value. The actual flow rate is also calculated and updated in response to a pump motor velocity count signal and then used to find the pressure intersection point on the control curve at the actual flow rate. The actual sensed pressure is subtracted from the control curve intersection pressure point to produce a pressure error value.

The pressure error signal is then integrated and scaled to produce a flow control command. The integrator is subjected to a lower limit of zero, an upper limit equivalent to the maximum flow rate, and a rate of change limit to produce an adjusted flow control command which is applied as a flow rate command to a digital feedback flow rate control servo loop.

A forward portion of the servo loop includes a flow rate error integrator, a sealer and a D-A converter coupled to apply an integrated flow rate error signal to a pulse width modulated (pwm) motor control system which is itself a high bandwidth servo loop and drives the pump motor. A velocity signal from the pump motor is provided as feedback to the pwm motor control system and through a compensating lead lag circuit to provide the updated flow rate values which are used in accessing the flow rate limit curve and in determining the flow rate error signal in the flow rate servo loop. Actual flow rates and actual pressures contain scaling errors due to tubing geometry and hardness, and pressure sensor scale errors. However, since the system adapts by measuring a zero flow point and a second flow point with substantially the same scaling errors as are experienced at other flow rates and corresponding pressures, these errors are substantially eliminated, to the extent that the scaling errors are linear functions. That is, the system operates in its own flow and pressure units which are determined by the instant tubing and pressure sensor involved. Compensating corrections for pump or tubing nonlinearity may also be provided for large negative pressures wherein the polyvinylchloride tubing, has a relatively low hardness, tends to flatten somewhat within the peristaltic roller pump and therein exhibits a correspondingly somewhat reduced flow rate than that which is calculated from an ideal linear extrapolation of data measured at lower magnitude negative pressures.

BRIEF DESCRIPTION OF THE DRAWINGS

A better understanding of the invention can be had from a consideration of the following detailed description, taken in conjunction with the accompanying drawings in which.

DETAILED DESCRIPTION OF AN ILLUSTRATIVE EMBODIMENT

The detailed description set forth below in connection with the appended drawings is intended merely as a description of an illustrative embodiment of the invention, and is not intended to represent the only form in which the present invention may be constructed or utilized. The description sets forth the functions and sequence of steps for construction and implementation of the invention in connection with the accompanying figures. It is to be understood, however, that the same or equivalent functions and sequences may be accomplished by different embodiments that are also intended to be encompassed within the spirit and scope of the invention.

Figure 1:
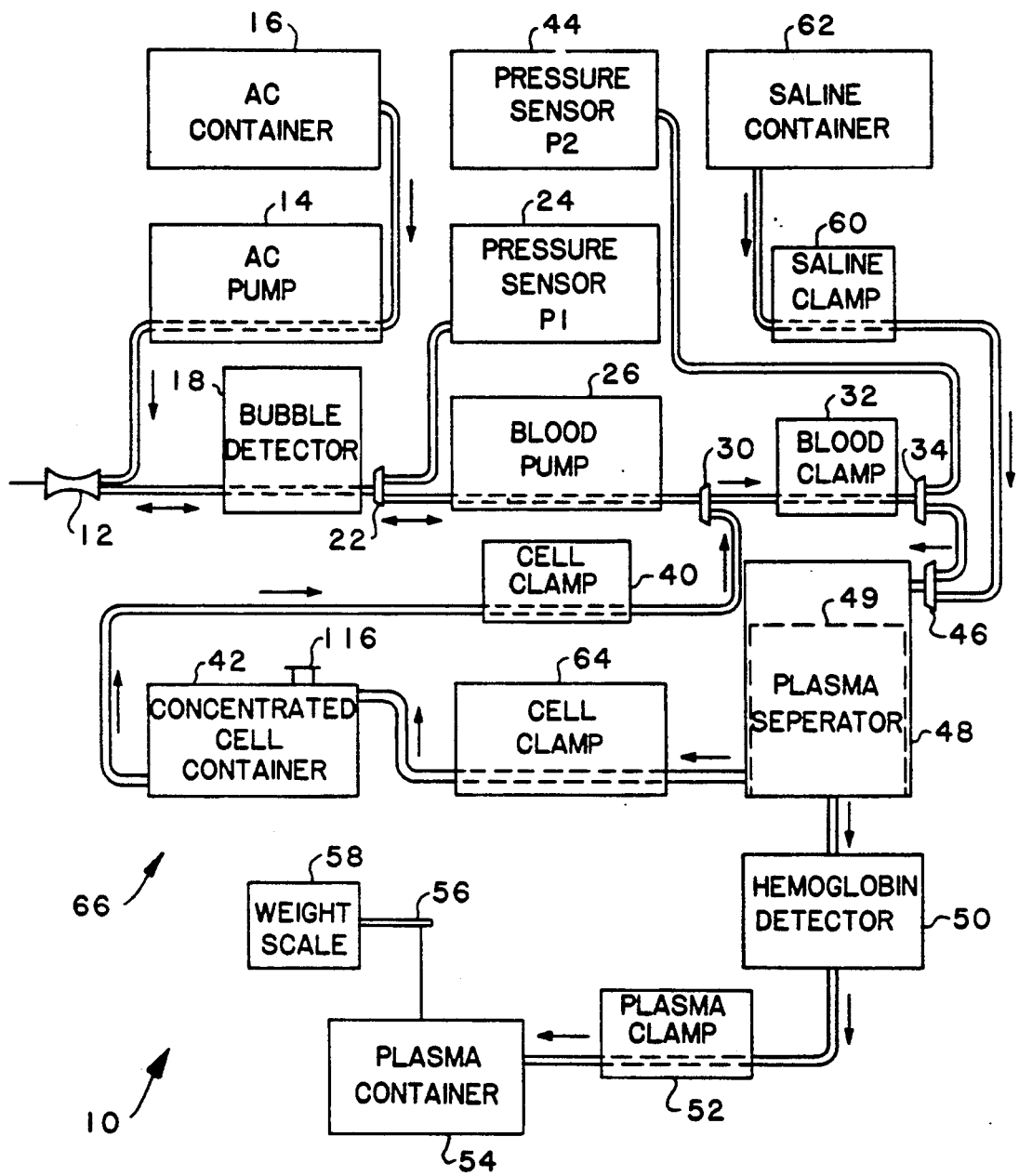
FIG. 1 is a schematic and block diagram representation of a fluid flow path for a plasmapheresis system using an adaptive body fluid flow control system in accordance with the invention.

Referring now to FIG. 1, there is illustrated a noninvasive, sterile plasmapheresis flow path 10 for a plasmapheresis system utilizing an adaptive bodily fluid flow control system in accordance with the invention. Intravenous connection of the flow path 10 to a subject is provided by a bodily fluid flow channel connection such as a phlebotomy needle 12 which is suitable for insertion into a vein of a living (or deceased) subject to provide bidirectional communication (e.g. alternate withdrawal and infusion) of blood and/or other fluids between the subject and the flow path 10 of the plasmapheresis system.

The flow path branches immediately adjacent the needle 12 with one branch extending through a noninvasive peristaltic anticoagulant pump 14 to an anticoagulant container 16. During a whole blood extraction cycle the anticoagulant pump 14 operates to supply and mix a small percentage of anticoagulant with the blood as it is being extracted to prevent activation of clotting mechanisms to prevent clotting and clinging of the blood to tubing sidewalls as it passes through the flow path 10. By mixing the anticoagulant with the whole blood at the needle 12 during extraction, the two fluids become fully mixed and less anticoagulant is required. This is a desirable effect which helps minimize the amount of anticoagulant in the separated plasma.

The other branch of the blood flow path 10 extends through a bubble detector 18 to another branch point 22. From branch point 22 one branch extends to a P1 pressure sensor 24 coupled to sense fluid pressure on the subject side of a blood pump 26. The pressure sensor 24 includes a disposable filter coupling the sensor to a pressure sensor tube 28 so as to maintain a noninvaded sterile atmosphere within the flow path 10. The second branch from branch point 22 extends through the noninvasive, peristaltic blood pump 26 to a branch point 30.

From branch point 30, one branch extends through a blood clamp 32 to another branch point 34. The other flow path at branch point 30 extends through a cell lamp 40 to the bottom of a concentrated cell container 42 which receives, and temporarily stores pending reinfusion, high hematocrit blood after a substantial portion of the plasma has been separated therefrom.

From branch point 34, one path extends to a second, P2 pressure sensor 44 while the other path extends through a branch point 46 to a plasma separator 48 which encloses a filter 49.

While the exact nature of the plasma separator 48 is not material to the present invention and can be fully conventional if desired, a highly advantageous plasma separator is a rotating filter type of separator as illustrated in Application Ser. No. 591,925 filed Mar. 21, 1984 for "Method and Apparatus for Separation of Matter From Suspension" by Donald W. Schoendorfer. For this type of separator the end product plasma output is coupled through a hemoglobin detector 50 and a plasma clamp 52 to a plasma container 54 which is maintained at atmospheric pressure. The plasma container 54 is suspended from a tension arm 56 to a weight scale 58 which provides feedback to the plasmapheresis system of the amount of plasma within container 54. Since P2 pressure sensor 44 is coupled to the inlet of plasma separator 48 and since the plasma outlet of separator 48 is maintained at atmospheric pressure plus a small adjustment for vertical height differences, the pressure sensor P2 44 provides an indication of transmembrane pressure for the filter membrane within plasma separator 48. This transmembrane pressure indication can be useful in monitoring and controlling the operation of plasma separator 48.

Another flow path from branch point 46 extends through a saline clamp 60 to a saline container 62. This flow path enables the separator to be initially primed with a small amount of saline prior to initial use, to be cleansed with saline after final use, and provides a flow path of saline solution from the saline container 62 through branch point 46 to branch point 34 and then through blood clamp 32 to blood pump 26 and bubble detector 18 to phlebotomy needle 12. This path enables saline solution to be communicated to the subject at the end of a plasmapheresis operation to provide fluid replacement of any plasma removed from the whole blood of the subject.

A cell pump 64 is coupled between an outlet of plasma separator 48 on the same side of the membrane as the inlet at the top of concentrated cell container 42. Cell pump 64 thus controls the flow of high hematocrit blood from plasma separator 48 to concentrated cell container 42 where the high hematocrit blood is temporarily stored during an extraction subcycle. Whenever the concentrated cell container 42 becomes full, a reinfusion subcycle is executed in which cell clamp 40 is opened blood clamp 32 is closed, and blood pump 26 is operated in the reverse direction to transfer the high hematocrit blood from concentrated cell container 42 back to the subject through bubble detector 18 and phlebotomy needle 12.

The entire bodily fluid flow path 10 including all of the branch points 22, 30, 34, 46 and the interconnecting tubing 66 are comprised of inexpensive, disposable materials which may be presterilized. The blood flow path is maintained completely noninvasive so as to protect against contamination and prevent and maintain sterility of the bodily fluids. The non-hardware portion of the flow path may be fully replaced for each different subject. Even the plasma separator 48 may be constructed such that only a sterile, disposable portion comes into contact with the bodily fluids. The risk of transmitting disease to the subject during the plasmapheresis operation is thereby minimized.

In order to optimize use of the plasmapheresis equipment and maintenance personnel while minimizing inconvenience and discomfort to the donor subject, it is desirable to accomplish a plasmapheresis procedure as rapidly as possible. Typically, the factor which limits the plasmapheresis operating rate is the intravenous blood volume and/or intravenous flow rate within the blood vessel from which blood is being extracted and/or into which blood is being infused. It is desirable to continually attempt to withdraw blood from the blood vessel at a relatively fast rate (e.g. 150 ml/min.) and, indeed, experience has taught that many human subjects are able to withstand and support consistent withdrawal and/or infusion of fluids at such relatively high rate (e.g. 150 ml/min.) without any incidence of vein collapse or regional depletion of available intravascular volume. However, even when momentary depletion or diminution in the available intravascular volume is observed, it is desirable to effect short term downward adjustments or pauses in withdrawal/reinfusion rate, but thereafter, to once again attempt to increase the withdrawal/infusion rate toward a predetermined maximum (e.g. 150 ml/min.) so as to effectively challenge the system and the donor to accomplish the withdrawal/reinfusion at the fastest possible rate for that particular human subject, under the then present conditions.

The adaptive blood flow control system of the present invention is operable to determine the maximum available flow rate for either extraction or reinfusion and to control the operation of the blood pump 26 such that the blood pump will operate either at a reduced maximum rate (e.g. less than 150 ml/min.) or at a preset maximal flow rate (e.g. 150 milliliters per minute) if the donor subject can accommodate such preset maximum rate. Additionally, the present invention is operable to rapidly and frequently rechallenge the human subject to increase a previously reduced maximum rate (e.g. less than 150 ml/min.) upwardly so as to continually attempt to maintain a flow rate as close to the preset maximal flow rate (e.g. 150 ml/min.) as possible.

A vein supplying or receiving intravenous bodily fluids through the phlebotomy needle 12 can be analogized to a small diameter, thin walled, rubber tube. Normally, the body maintains a pressure within the vein of approximately 6 mm. Hg. above atmospheric. This is sufficient to maintain the vein expanded and permit normal blood flow. However, if blood is extracted faster than it can be supplied by the vein, the pressure within the vein drops toward atmospheric, causing the external atmospheric pressure against the body to collapse the vein. Blood flow can be reinstated by terminating pumping through the needle until normal vein pressure is restored within the vein. However, frequently the sidewalls of the vein engage the end point of the phlebotomy needle as the vein collapses to thereby occlude blood flow through the needle. Even as the vein reexpands, the needle may remain occluded against the vein wall and it then becomes necessary to reposition the needle. This of course imposes considerable time delay and may cause donor anxiety.

During reinfusion care must also be taken to assure that the bodily fluid flow rate is not too great. If the flow rate is too great, pressure rises within the vein until the bodily fluids either begin to leak through the seal point between the needle and the vein sidewall or expand the vein until a break occurs. In either case, bodily fluids leak into the body tissues surrounding the vein to create an undesirable and even potentially dangerous hematoma.

During venepuncture it is common to place a pressure cuff around the upper portion of the subject's arm with a pressure of about 60 mm Hg to make the vein more visible. After venepuncture the pressure within the cuff is reduced to about 40 mm Hg during extraction and to substantially 0 during reinfusion. Thus, the 0 flow rate (through needle 12) internal vein pressure will be determined largely by the cuff pressure during extraction and will be approximately 40 mm Hg. The best way to optimize the extraction flow rate would no doubt be to sense actual internal vein pressure and limit flow rate to a magnitude at which actual vein pressure begins to approach atmospheric pressure. However, measurement of actual vein pressure is not practical without multiple needle procedures or expensive concentric dual needles. The present invention uses measurements at pressure-flow rate test points between the needle 12 and blood pump 26 to generate an estimate of what pressure the maximum flow rate will produce, based upon extrapolation of the measured curve for substantially linear pressure flow relationships and non-linear pressure flow relationships when nearing saturation, i.e. pressure drop, due to subject flow limitations.

Figure 2:
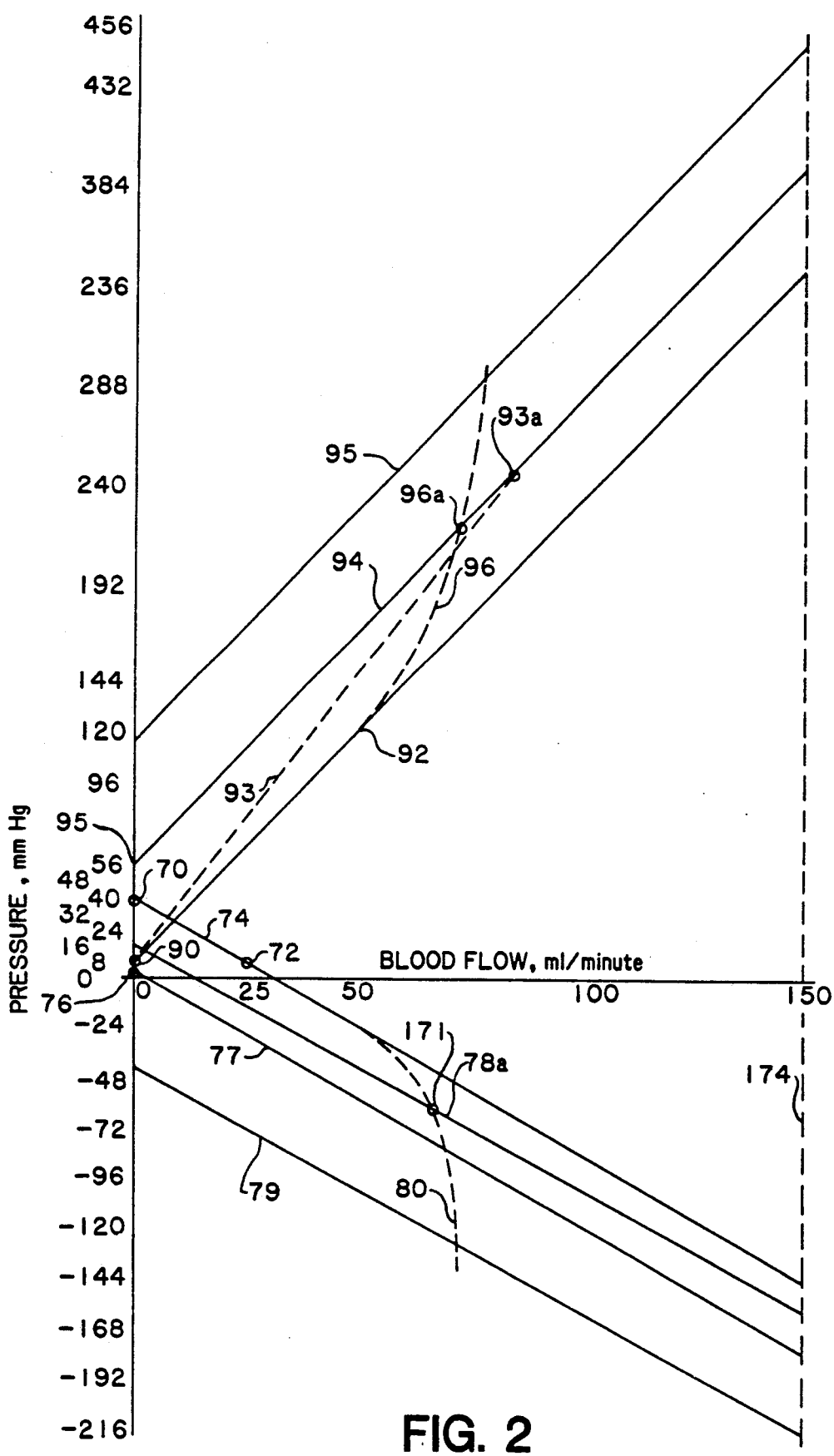
FIG. 2 is a graphical illustration of flow rate curves and control curves for extraction and reinfusion.

Referring now to FIG. 2, in establishing the control limit curve for extraction the adaptable flow rate control system samples the pressure at a 0 flow rate at point 70. With the pressure cuff inflated to a typical 40 mm Hg it would be expected that point 70 would also occur at approximately 40 mm Hg, adjusted for any gravitational effect upon the static blood within the tubing (taken as zero in the example below). For the second test point, the blood pump 26 is commanded to operate at a rate corresponding to 25 ml per minute, which is expected to be within the flow rate capability of virtually all subjects. In our present example the second test point occurs at a flow rate of 25 ml per minute and a pressure of 8 mm Hg relative to atmospheric pressure. If it is assumed that the subject is readily capable of providing the 25 ml per minute flow rate then the pressure difference between test point one at 70 and test point two at 72 is due to a loss induced pressure drop in the fluid flow path between the vein and the pressure sensor branch point 22. This pressure drop is due primarily to fluid flow through the constriction of the needle 12 which is dependent upon needle size, blood viscosity and flow rate. For a given plasmapheresis session the needle size parameters remain substantially constant and the pressure drop between the vein and the P1 sensor 24 is substantially proportional to fluid flow rate and viscosity. The adaptive flow control system takes advantage of this linear relationship by linearly extrapolating the pressure data from test points 70 and 72 at the beginning of each extraction subcycle, to generate a full vein pressure flow rate curve 74. The full pressure curve 74 is then translated downward by an amount equal to a difference in pressure between the 40 mm Hg pressure at 0 flow rate pressure at the first test point 70 and a minimum acceptable internal vein pressure such as 4 mm Hg at point 76 to generate a translated flow rate limit curve 77. The translated flow rate limit curve 77 thus has the general format of $$P = \{[P(2)-P(1)]/[FR(2)-FR(1)]\} \times FR + 40 - 36,$$

where P is the instantaneous pressure, P(2) is the sensed pressure at test point 2, P(1) is the sensed pressure at test point 1, FR(2) is the flow rate at test point 2, FR(1) is the flow rate at test point 1, FR is the instantaneous flow rate, 40 is the zero flow rate sensed pressure intercept or full vein pressure and −36 is the maximum allowable intravenous pressure drop within the vein to prevent vein collapse at any flow rate. Thus the region between curve 72 and curve 77 is the region of allowable steady-state operation.

In a practical system it is necessary to provide margin for noise, drift and dynamics. The control curve 78A is raised above curve 77 and rotated counter-clockwise to provide margin at low blood flow and somewhat higher margin at high blood flow rates.

The control curve 78A thus has the general format of $$P = \{([P(2)-P(1)]/[FR(2)-FR(1)] + 12/FR(3)\} \times FR + 40 - 36 + 20$$

which may be given different values and the +2/FR(3) corresponds to a decrease in slope.

As measured at P1 pressure sensor 24 the actual sensed pressure will follow a curve 80 which will substantially follow flow rate curve 74 so long as the subject is able to supply the amount of blood being withdrawn. However, as the amount of blood withdrawn approaches the maximum accommodation rate, the internal vein pressure will begin to drop and this pressure drop will be superimposed upon the pressure drop across the needle so that actual flow rate curve 80 will begin to decrease in pressure more rapidly than flow rate curve 74. The adaptive blood flow control system uses P1 pressure sensor 24 to monitor the actual pressure of flow rate curve 80 and when curve 80 crosses extraction control curve 78A, the error signal within the control system, described below, changes polarity and drives the blood pump toward reduced flow rate. The adaptive blood flow control system then operates to maintain system operation at the point at which actual flow rate curve 80 crosses extraction flow rate limit curve 78A so long as this crossover point 82 is less than a flow rate limit shown in FIG. 2 as the maximum flow rate limit of 150 ml per minute. The maximum nominal flow rate of 150 ml per minute. The flow rate limit will be pumped so long as the subject is able to accommodate this flow rate limit.

Where pressure curve 80 crosses over and becomes more negative than control curve 78A, the vein is close to experiencing an occlusion. As discussed above, translated flow rate limit curve 77 represents the limit somewhat below which vein occlusion will occur. An alarm limit curve 79 which may be parallel or non-parallel to the control curve 78A is positioned 60 mm Hg below the control curve. When the extraction blood flow rate substantially exceeds the flow supply to the vein an occlusion will occur. It is then necessary to pause the separation process and obtain the attention of the operator in order to determine if the venipuncture is sound. Transient flow rates causing pressure curve 80 to cross translated flow rate limit curve 77 should be avoided if possible.

At the start-up of the process the steady-state donor vein flow supply is not known and yet it is desirable to rapidly accelerate the blood flow toward the maximum limit of 150 ml/minute to avoid wasted time for subjects who are able to operate at relatively high flow rates.

Figure 8:
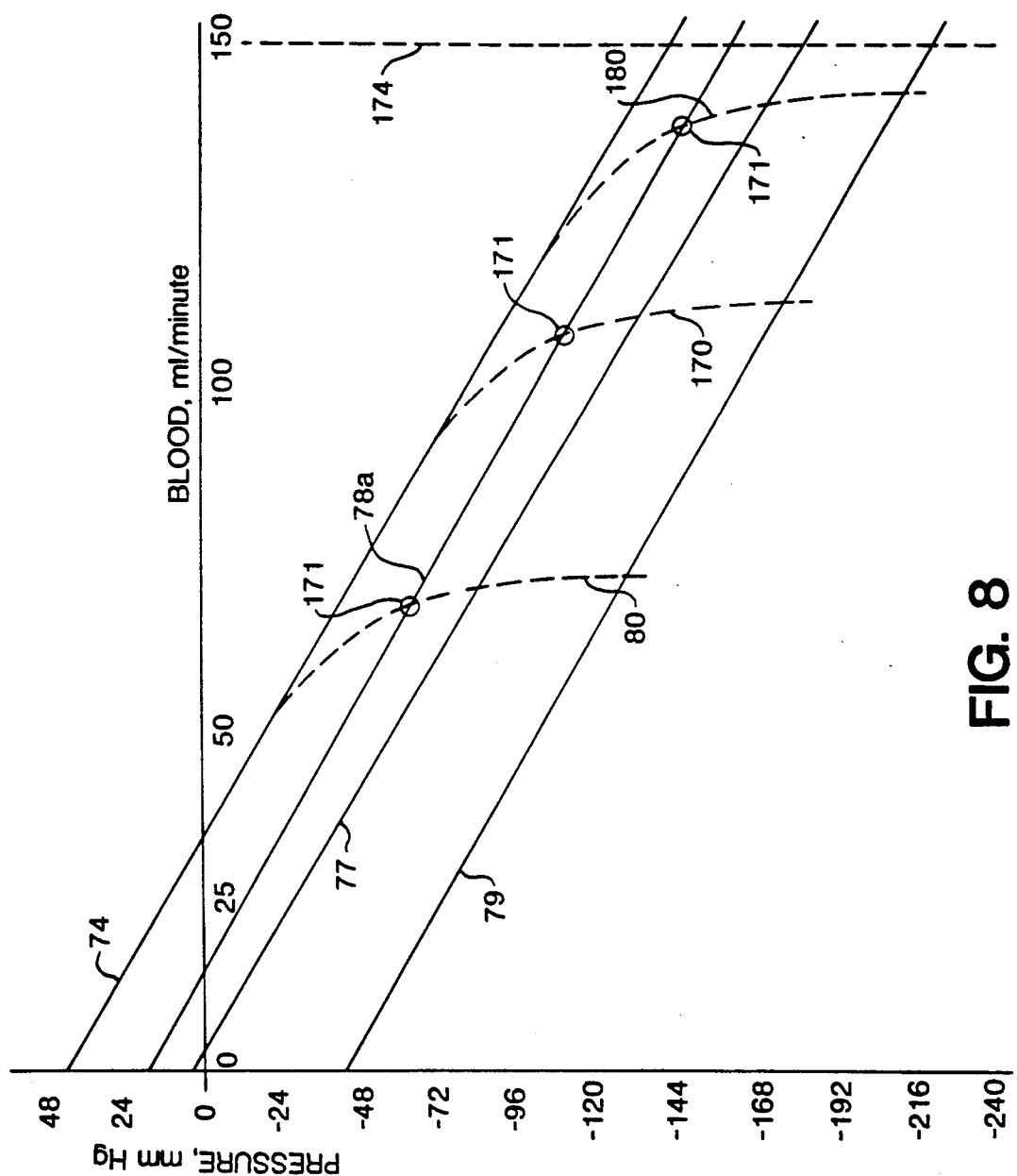
FIG. 8 is a graphical illustration of an extraction flow rate limit curve and several steady-state flow supply curves.

FIG. 8 illustrates a relatively low steady-state vein flow supply curve 80, an intermediate steady-state vein flow supply curve 170, and a relatively high steady-state vein flow supply curve 180.

Figure 9:
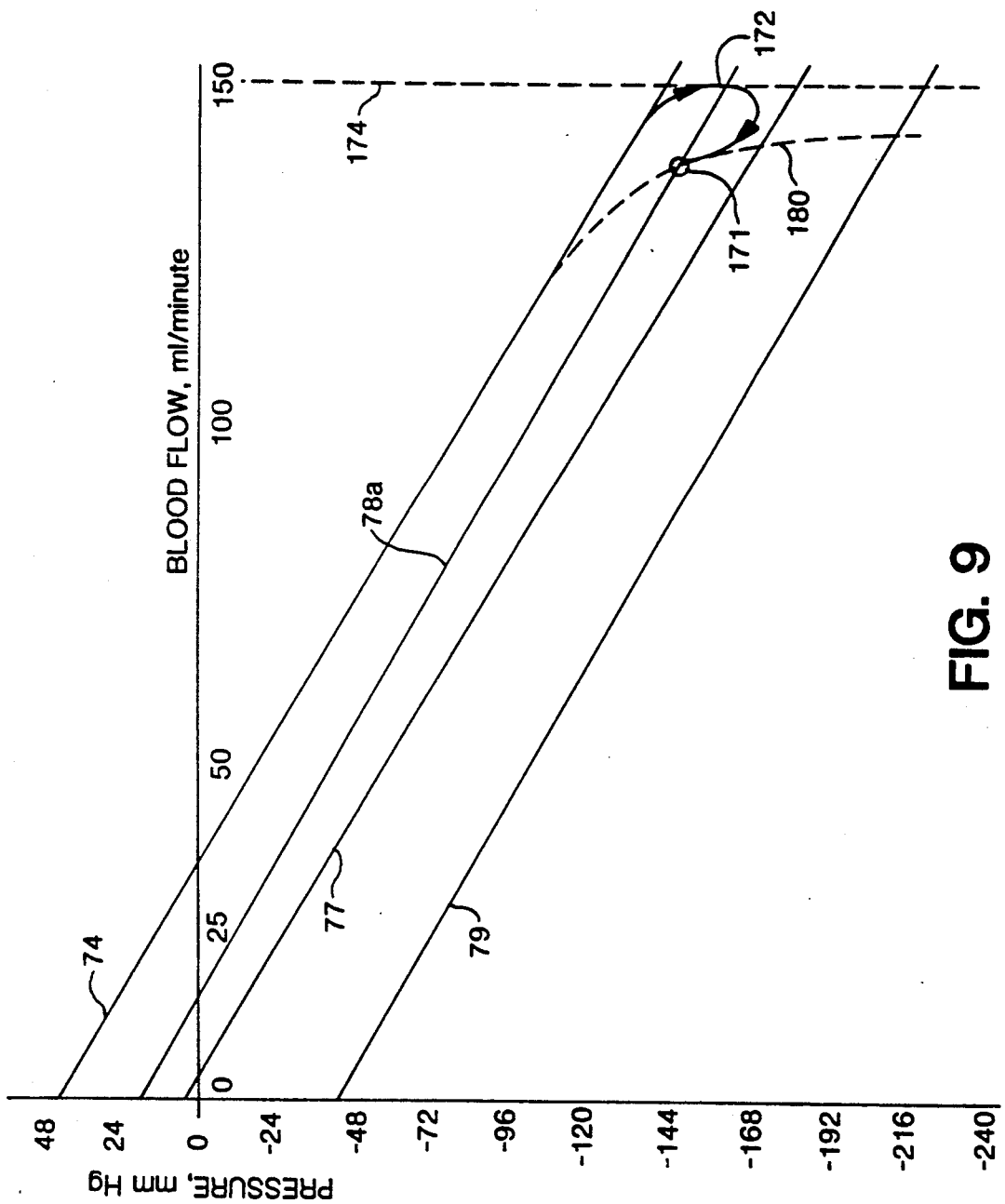
FIG. 9 is a graphical illustration of a high steady-state flow supply subject and a transient path locus of operating points following a blood pump start-up.

Momentarily a vein is able to sustain substantially higher flow rates than steady-state vein input flow rates due to the local volume contained within the vein in the region of the needle. At start-up, for example, for a donor able to supply a steady-state flow rate consistent with curve 180, for a short time it would be possible to extract at a rate of 150 ml/minute. If the donor input flow rate is close to 150 ml/minute then when the local volume contained within the vein in the region of the needle becomes depleted, the pressure rapidly drops, and the blood pump is decelerated back toward the steady-state flow supply curve 180 through action of the control system. This start-up transient flow characteristic, which is a locus of operating points shortly after blood pump start-up, is illustrated as transient path 172 in FIG. 9.

The dynamics are such that with a maximum flow limit of 150 ml/minute and a steady-state flow supply according to curve 180, the most negative excursion of transient path 172 does not encounter the translated flow rate limit curve 77 and therefore the pressure within the vein in the region of the needle does not fall below atmospheric pressure and the vein does not collapse and flatten.

Figure 10:
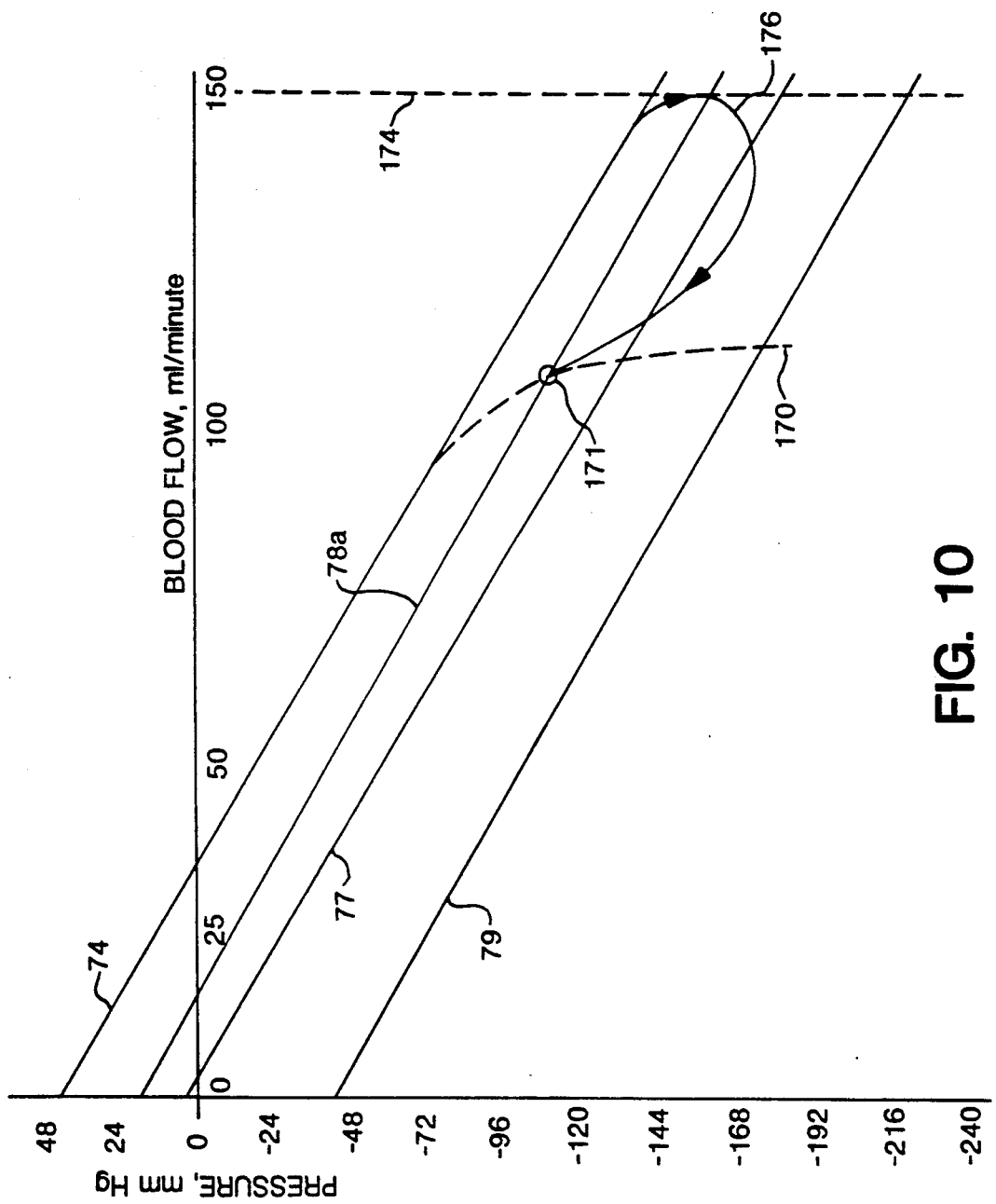
FIG. 10 is a graphical illustration of an intermediate steady-state flow supply subject and a corresponding transient path.

The situation is markedly different for an intermediate steady-state blood supply donor as depicted in FIG. 10 with an intermediate steady-state blood supply curve 170 and the maximum flow rate limit 174 of 150 ml/minute. The locus of points shortly after start-up for this situation is shown as transient path 176 in FIG. 10. Since transient path 176 crosses over and substantially below the translated flow rate limit curve 77, the vein collapses and an occlusion occurs. Depending upon the duration of path 176 below curve 77, the system may or may not recover without stopping and pausing while the vein refills.

Figure 11:
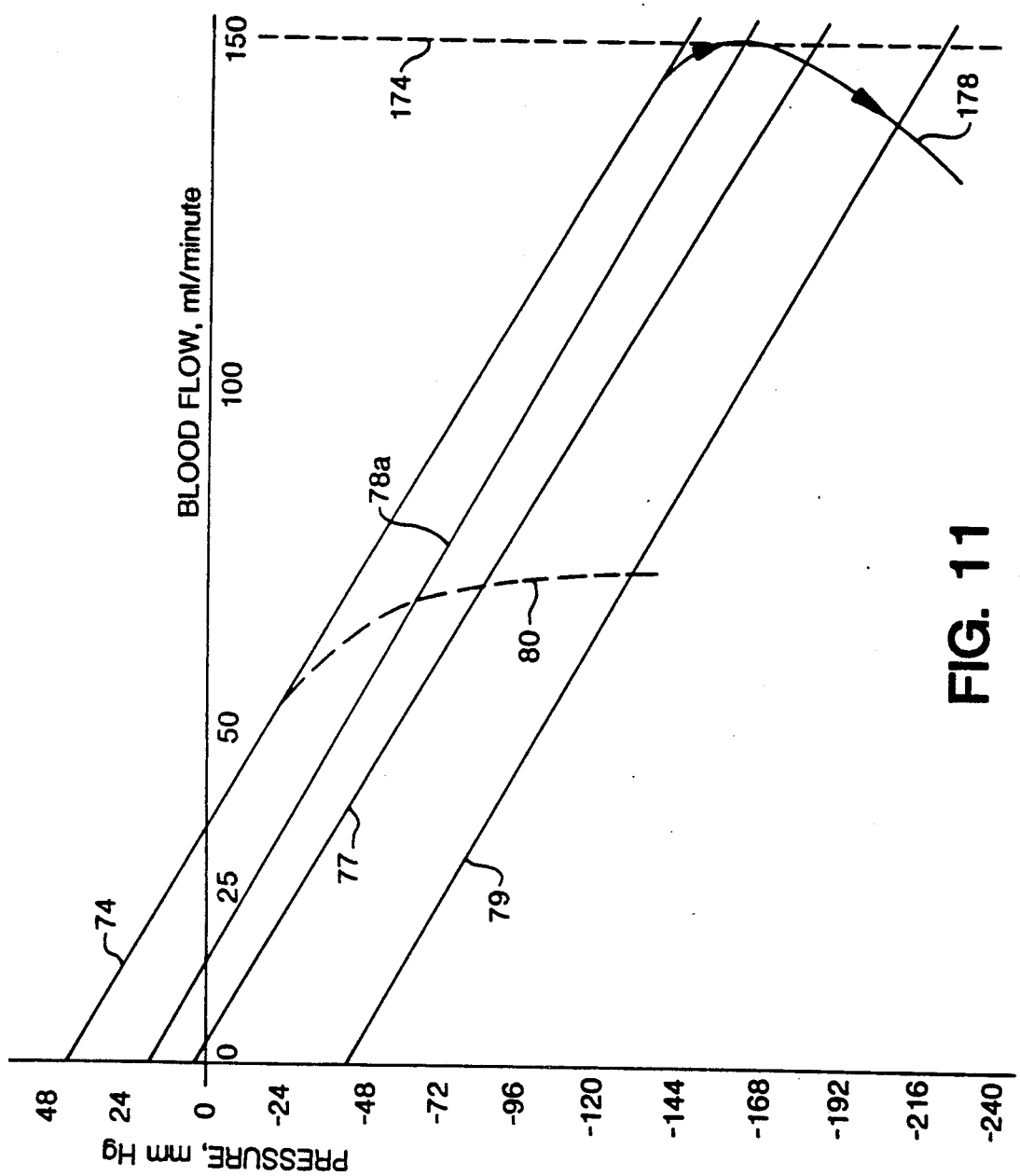
FIG. 11 is a graphical illustration of a low steady-state flow supply subject and a corresponding occlusion transient path.

For the situation of low steady-state vein supply 80, an occlusion would generally occur if the maximum flow rate limit is left at 150 ml/minute, and the locus of operating points shown as transient path 178 in FIG. 11, would ross over curve 77, and the alarm limit 79, and occlude the vein, requiring a quick stop of the blood pump and a pause in the procedure with resulting loss of time and requiring operator involvement.

Figure 12:
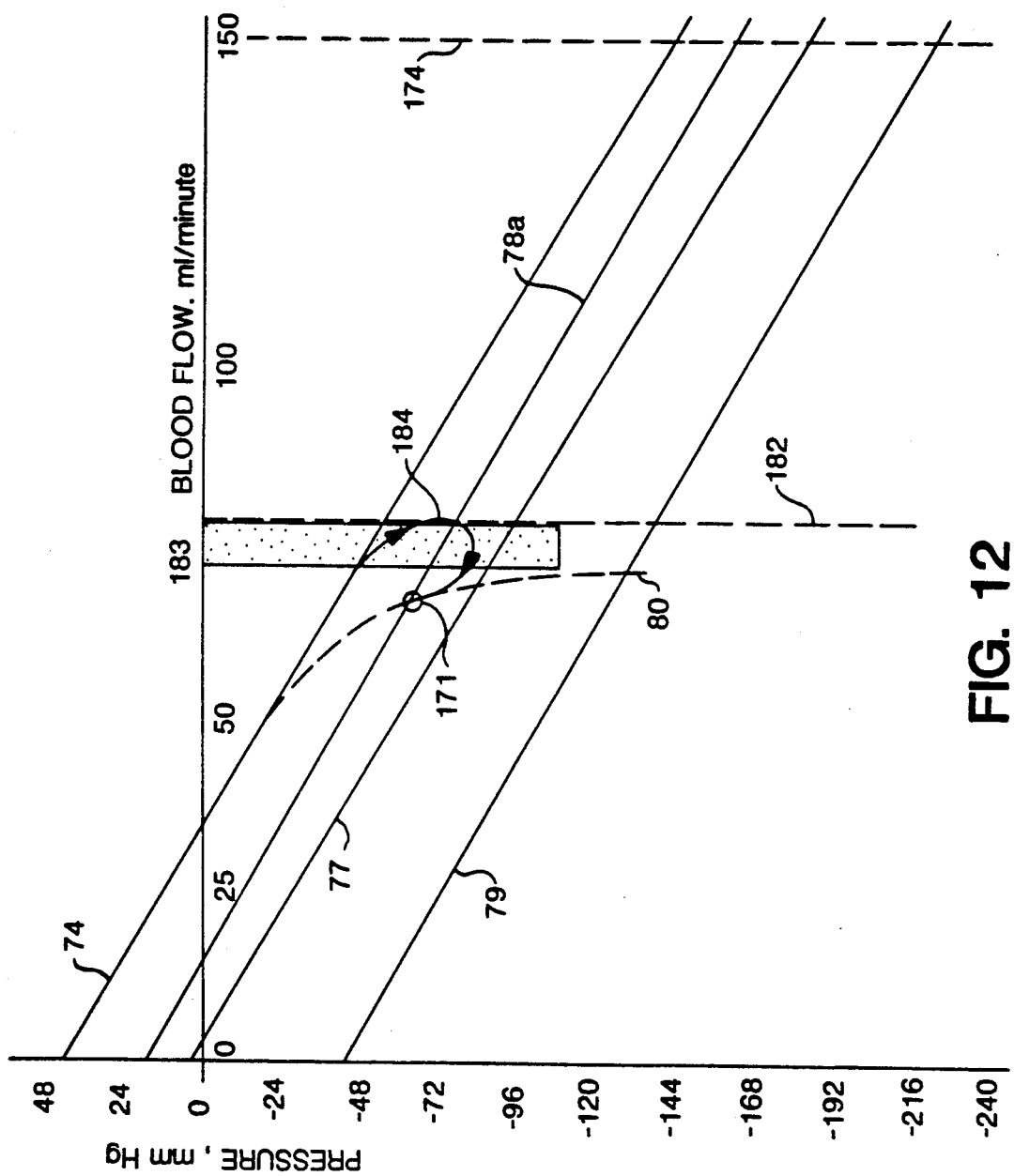
FIG. 12 is a graphical illustration of a low steady-state flow supply subject and a transient path utilizing an adaptive flow rate limit.

An adaptive flow rate limit 182 is shown in FIG. 12 in which the transient path following a start-up of the blood pump for a low steady-state vein supply (curve 80) is less severe and does not cross over curve 77. Adaptive flow rate limit 182 is a floating flow rate limit that adapts to the flow rate available, as further described below. The adaptive flow rate limit serves to prevent greatly excessive extraction blood flow beyond the steady-state vein supply, providing a lower depletion rate of the local vein volume in the region of the needle, thereby allowing time for the control system to adjust the blood pump without vein occlusion.

A reinfusion flow rate limit curve can be determined for reinfusion in substantially the same manner as for extraction. Pressure can be sensed at first and second flow rate test points, for example a first test point 90 (FIG. 2) at a flow rate of 0 and a second test point at a flow rate which is considered to be well within the return flow rate accommodation of any subject. Because the pressure cuff is depressurized for reinfusion, the 0 flow rate ordinate intercept test point 90 will normally be at approximately 6–8 mm Hg, which is the normal intravenous blood pressure. Two-needle procedures in which the extraction and reinfusion needles may be of different gauge (internal diameter) benefit through the taking of independent measurements of the extraction and reinfusion slope characteristics with accompanying adjustments of the extraction and reinfusion flow rates (i.e. pump throughputs) according to approximate changes in viscosities and/or other variables.

In particular, one type of withdrawal/reinfusion procedure known as therapeutic plasma exchange, involves (a) withdrawal of whole blood, (b) separation and removal of autologous plasma from the blood, (c) replacement of the removed autologous plasma with a quantity of inert diluent or donor plasma and (d) reinfusion of the patient's blood cells plus the added inert diluent or donor plasma. In such therapeutic plasma exchange procedures, it will be appreciated that the hematocrit and/or viscosity of the withdrawn whole blood may differ substantially from the hematocrit and/or viscosity of the resuspended blood cells being reinfused into the patient. Thus, in such procedures, it is highly desirable to separately monitor, adjust and control the withdrawal and reinfusion flow rates so as to accommodate the diffusing viscosities of the fluids being withdrawn and reinfused.

Even in standard plasmapheresis procedures wherein a quantity of plasma is removed and the remaining blood cell concentrate is reinfused, the preferred method of return cell flow control assumes a predetermined approximate increase in viscosity due to the removal of plasma, such as a doubling of viscosity. The slope of the predetermined viscous pressure drop curve found for extraction is therefore increased by multiplying by a slope factor of 1.5 to 3.0 (2.0 being presently preferred) and its sign is changed to provide the reinfusion pressure control curve slope. Calculations of the slope factor may be made using return fluid viscosity estimations based on estimation algorithms or may utilize actual measured viscosity values. The relative viscosities of the fluids may vary depending on what fluid is being returned to the patient/donor (e.g. saline, blood cell concentrate, albumin, resuspended blood cell concentrate, etc.).

Normally, the peripheral vein into which fluids are reinfused will accommodate small overpressures during reinfusion. On the other hand if withdrawal of blood from the vein occurs at a rate which is only slightly too fast for the available intravasoular blood volume, the pressure within the vein will fall below the ambient pressure and the vein will collapse. Therefore because fluid reinfusion requires less rigid control of the fluid flow rate, a significant positive offset (e.g. 48 mm Hg) at zero flow is allowable. With knowledge of the instant approximate relative viscosity of the return fluid, a therapeutic plasma exchange system, not shown, may be optimized by adjusting the above slope factor according to the combined viscosity of the mixture of concentrated red cells and replacement fluid.

In the present example, the needle-concentrated cell flow relationship can then be represented by normal vein pressure flow rate curve 92 of FIG. 2 wherein point 90 is the zero flow vein pressure without pressure cuff. In this example the slope of full vein pressure flow rate curve 72 is multiplied by $-2.0$ to obtain the slope of reinfusion normal vein pressure flow rate limit curve 92. Translating flow rate curve 92 upward by 48 mm Hg produces a reinfusion control curve 94 having a 56 mm Hg zero flow rate intercept at point 95. Control curve 94 becomes the final reinfusion control curve to limit the actual pumping rate. The summing point 95 on control curve 94 is the result of offsetting positively by 48 mm Hg, changing the sign of, and increasing the slope of curve 74 by a factor of two.

A curve 93 represents actual sensed pressure in a hypothetical case wherein the concentrated cells are sufficiently viscous to cause somewhat reduced flow at the stabilizing intersection point 93A with curve 94. This reduced flow can be a benefit since for excessively high flow rates of highly viscous fluids, the fluid shear may become excessive and damaging to red blood cells.

This method of generating a reinfusion control curve from the extraction curve 74 has the added advantage that the blood pump is not required to pause for an intermediate measurement since the needle and source blood characteristics are determined in the extraction measurement. If the incoming blood from the subject is of relatively low hematocrit, such as 30, the control curve 94 slope will be relatively small, and the 48 mm offset will allow the return cell hematocrit (and therefore viscosity) to be substantially increased over the incoming blood hematocrit while continuing to allow high flow rates. But for relatively high hematocrit incoming blood, such as 45, the control curve 94 slope will be relatively steep so that the 48 mm offset will be relatively insignificant and not allow much more than a doubling of viscosity without a reduction in return flow rate to save the return cells from exposure to excessive shear. Other methods using estimates or measurements of relative viscosity and adjusting the slope accordingly are within the scope of this invention.

Curve 96 of FIG. 2 illustrates a hypothetical actual flow pressure curve having a nonlinearity which would occur if return flow restriction occurs or if the needle slipped into the flesh and a free return flow was inhibited. This situation would normally cause the potential of a hematoma formation The intersection of curve g6 with curve 94 at point 96A reduces return cell flow to accommodate reduced flow capacity. Rapid increases in pressure beyond curve 94 cause total pump shutdown through a comparison of the actual pressure (curve 96) and a threshold curve offset and above curve 94 by a pre-determined amount, such as 60 mm Hg, as shown by reinfusion alarm limit curve 95. The threshold may be a function of blood flow rather than a fixed 60 mm Hg, and may involve various filter algorithms to improve the detection of an intrusion.

The control curve or flow rate limit curve 94 for reinfusion of concentrated cells thus has the general formula;

$$P = M \{[P(1)-P(2)]/[FR(2)-FR(1)]\} \times FR + 48 + 8$$

wherein M is a positive viscosity multiplying term applied to the negative of the extraction slope, and may take on other values, the +8 is the measured zero flow vein pressure, and the 48 is an offset from the measured zero flow vein pressure and may be assigned different values. The change in the sign of the slope is effected by subtracting P(2) from P(1) instead of P(1) from P(2).

The hypothetical actual donor subject concentrated cell flow rate curve represented for example by dashed line curve 93 illustrates the system flow rate limit function for reinfusion. The adaptive blood flow control system operates to reinfuse blood at as fast a rate as possible until up to a limit of the flow rate point at which the actual sensed pressure represented by curve 93 intercepts the control curve 94 or until the adaptive flow rate limit is reached, whichever is less. The system thus assures that the optimum flow rate is attained for extraction or reinfusion.

Figure 3:
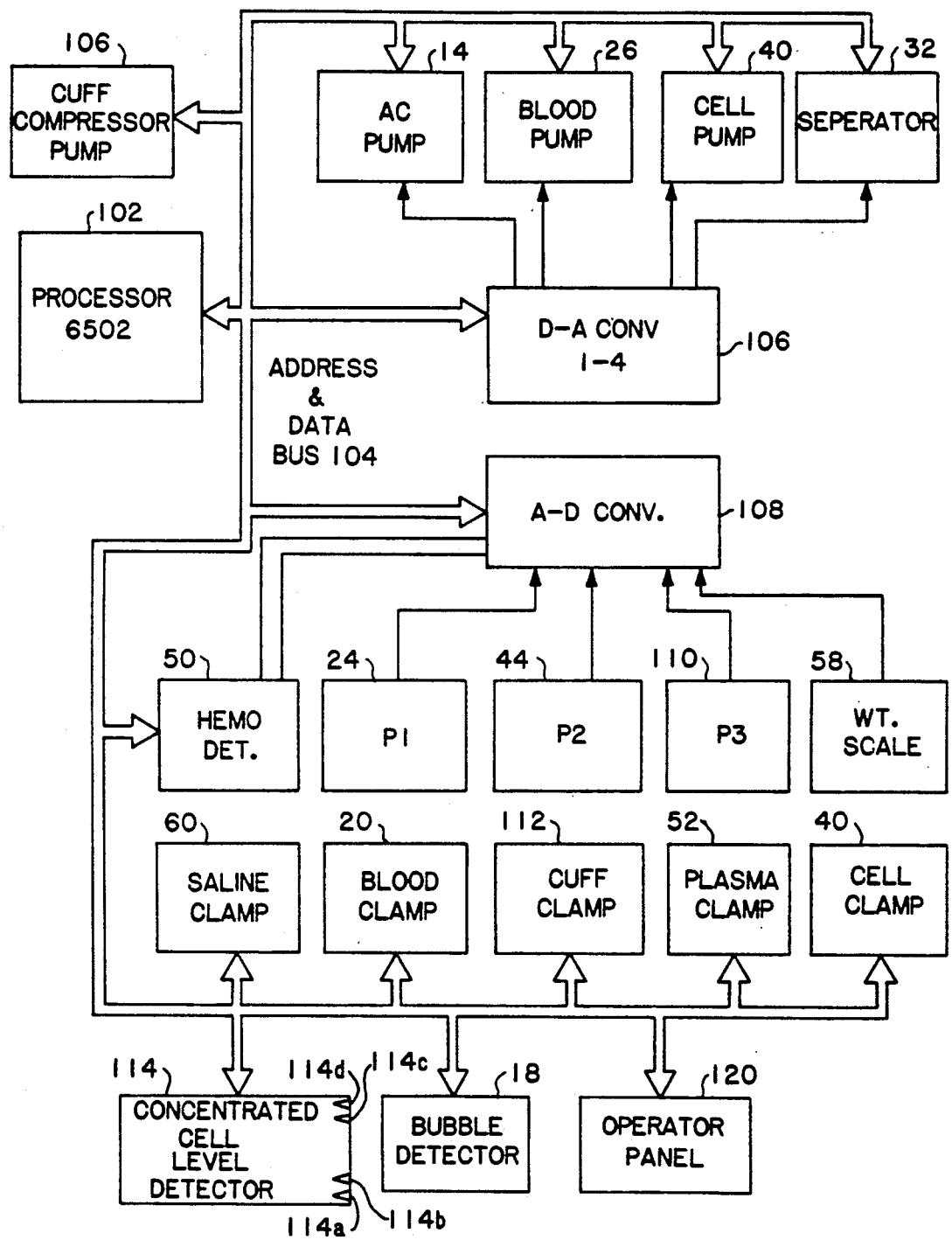
FIG. 3 is a functional block diagram representation of a plasmapheresis system incorporating an adaptive blood flow control system in accordance with the invention.

Referring now to FIG. 3, plasmapheresis system 100 includes a processor 102 which maintains operational control over plasmapheresis system 100. In the present example processor 102 is a 6502 type of microprocessor and is deemed to include all of the memory and peripheral logic which is typically associated with a microprocessor to provide proper system operation. Processor 102 communicates with other portions of plasmapheresis system 100 through an address and data bus 104. Among the items coupled to address and data bus 104 is a cuff pressure pump 106. Cuff compressor pump 106 controls the pressure within the arm cuff which is utilized to increase intravenous pressure in a subject donor.

Also connected to memory bus 104 are the three fluid pumps, anticoagulant pump 14, blood pump 26, and cell pump 40, and the plasma separator 32. The commercially available motors driving the rotating portions of these devices each include Hall effect sensors which generate 12 position increment signals per motor revolution. These position feedback signals are accumulated by a resetable counter associated with each of the motors with the accumulated counts being periodically provided as position and velocity feedback over memory bus 104 to processor 102. A digital-to-analog converter 106 is also coupled to memory bus 104 to receive velocity commands from processor 102 for each of the motors associated with AC pump 14, blood pump 26, cell pump 40 and separator 32. Digital velocity commands received from processor 102 are converted to analog signals which are communicated to the respective motors.

An analog-to-digital converter 108 is connected for communication with processor 102 over memory bus 104. Analog-to-digital converter 108 receives analog information over up to 8 channels and conveys the information in digital form to processor 102. Among the devices providing analog signals to analog-to-digital converter 108 are the hemoglobin detector 50 which provides two channels of analog optical information which is sensitive to the appearance of red hemoglobin within the plasma, pressure sensor P1, pressure sensor P2, and a third pressure sensor P3 110 which is responsive to the pressure within the pressure cuff attached to the donor subject's arm. Each of the pressure sensors provides a single channel of input to analog-to-digital converter 108. Weight scale 58 provides another single channel of analog input to converter 108 to indicate the weight of the plasma and bag hanging from force arm 56 of weight scale 58. Each of the noninvasive fluid flow clamps including saline clamp 60 blood clamp 20, plasma clamp 52 and cell clamp 40, are coupled to receive digital clamping commands over memory bus 104 and respond thereto by opening or closing the flow path through the clamp in response to the received commands. Also coupled in a similar manner is a cuff clamp 112 which is disposed to selectively maintain or relieve air pressure within the pressure cuff attached to a donor subject's arm.

A concentrated cell level detector 114 is also coupled to communicate over memory bus 104 digital signals indicating the level of concentrated cells within concentrated cell container 42. In the present example the concentrated cell level detector 114 includes four optical sensors disposed to indicate whether or not the concentrated cell fluid is above or below a bottom sensor 104a disposed near the bottom of the concentrated cell container 42, above or below a next to bottom sensor 114b disposed a short distance above the bottom sensor 114a, above or below a top sensor 114d disposed near the top of concentrated cell container 42 to indicate a full condition, or above or below a next to top sensor 114c disposed a short distance below the top sensor 114d to indicate an almost full condition.

Bubble detector 18 is digitally coupled through memory bus 104 to processor 102 to provide an indication of any emergency condition in which a bubble is detected in the intravenous fluid flow line near the phlebotomy needle.

An operator panel 120 is also coupled over address and data bus 104 to processor 102. Operator panel 120 receives numeric commands as well as advance and stop or back commands to control the stepping of the operator through the various steps associated with plasmapheresis. The operator panel 114 also provides feedback information to the operator in the form of a display which indicates the status of the plasmapheresis operation.

Figure 4:
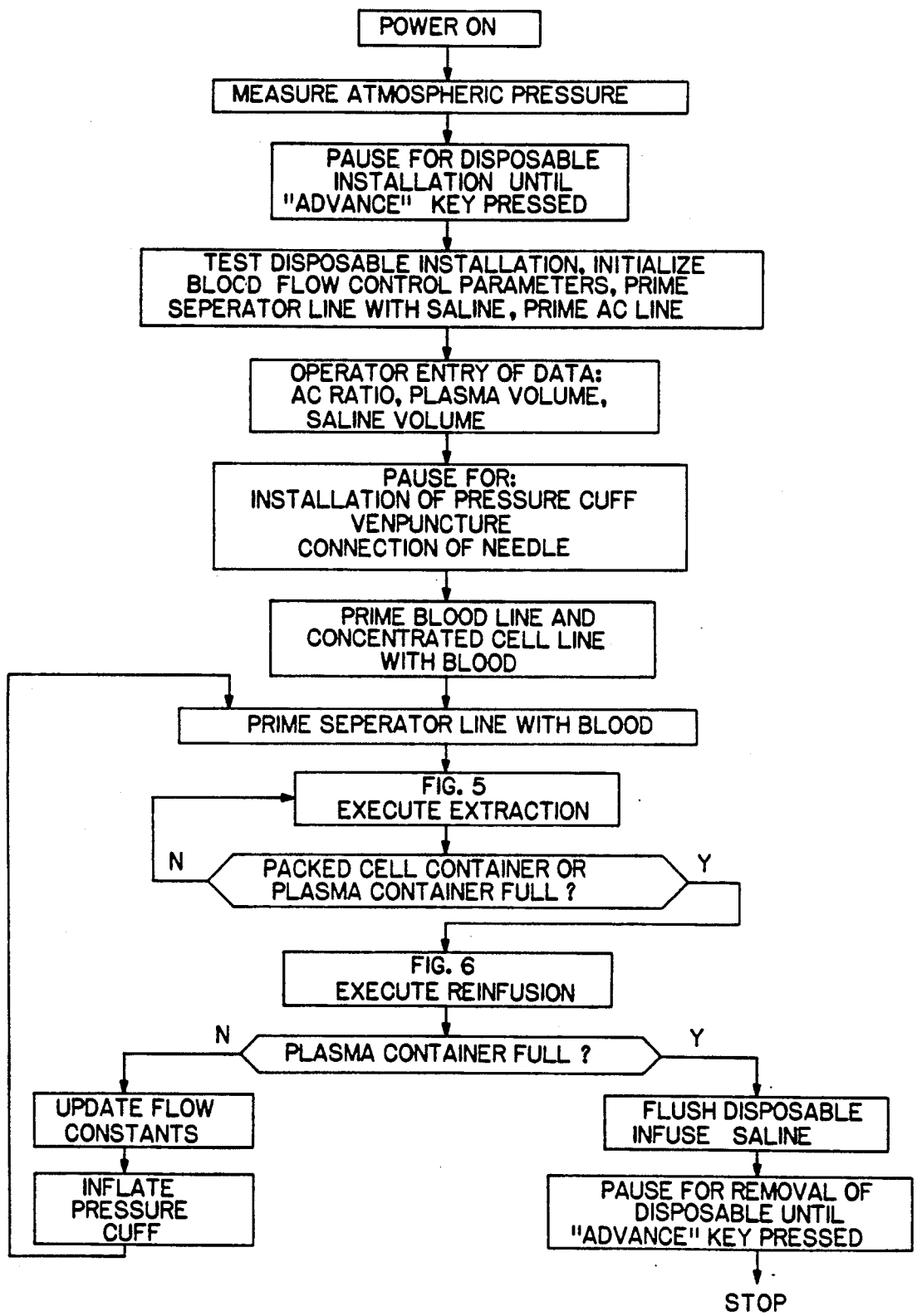
FIG. 4 is a flow chart illustrating a plasmapheresis operation.

A typical plasmapheresis operating cycle utilizing plasmapheresis system 100 is illustrated in FIG. 4. Following power turn-on or completion of a prior procedure, the system 10 uses P1 pressure sensor 24 to measure atmospheric pressure for use in calculating sensed pressure differences relative to atmospheric pressure. System 10 then pauses for installation of the disposable tubing, pressure sensor interfaces, plasma container 54, concentrated cell container 42 and separator filter 49 which form the sterile noninvasive fluid flow path shown in FIG. 1.

Upon completion of installation of the disposable apparatus the operator presses the ADVANCE key and the plasmapheresis system 100 progresses to a test and initialization step.

In the test and initialization step the system 100 uses the various pumps and clamps to pressurize the disposable tubing and test for any leaks. If any leaks are found the system stops and invites the operator to correct them through a display message. Assuming no leaks are found the system opens the saline clamp 60 for a short, predetermined period of time to allow the gravity feed of saline prime into the tubing leading to plasma separator 48 as well as a small space within plasma separator 48 between the peripheral wall and the filter membrane 49. During this procedure cell pump 64 is operated to draw air and eventually a small amount of saline solution from plasma separator 48 to concentrated cell container 42 where the air may be exited through a filtered vent aperture 116. Upon completion of the saline prime the anticoagulant pump 14 is operated to prime the tubing between anticoagulant container 16 and phlebotomy needle 12 with a predetermined volume of anticoagulant fluid.

Upon completion of the anticoagulant prime the system pauses and the display invites the operator to enter donor subject related information defining the desired volume of plasma to be collected and the volume of saline to be returned at the end of the procedure. Additional procedure-specific information may be entered at this time for the desired anticoagulant to blood ratio. If the operator enters no value, a predetermined default value is used.

Optional parameters may also include an operator selected maximum flow rate value less than the system maximum flow rate value of 150 ml/min. If the subject has a past history or some physical condition suggesting that the maximum flow rate should be reduced, this value can be entered at this time. The reduced maximum value may preclude the occurrence of an occlusion as the flow rate accelerates toward the default maximum value of 150 ml per min, or another selected initial lower value of the adaptive flow rate limit such as 120 ml/minute.

The data processor 102 stores and maintains three different flow rate limit values. The first is an absolute limit that is defined to be 150 ml per min and cannot be changed under ordinary circumstances. The second is the operator selected maximum flow rate value, which is constrained by system design to be between 30 and 150 ml per min. A default value of 150 ml per min is used if the operator does not enter a different value.

The third or adaptive flow rate limit value actually defines the flow rate limit which is controlling at any given time during the operation of the plasmapheresis system. The adaptive flow rate limit value may be automatically adjusted from time to time but is always constrained to be less than or equal to the operator selected maximum flow rate value. Any time the operator selected maximum flow rate value is updated by an operator the adaptive flow rate value is set to a matching value.

The operator may adjust the operator selected maximum flow rate value at any time during system operation by actuating a key on operator panel 120. The operator is then presented with a menu of available functions which include updating of the operator selected maximum flow rate value. If this option is selected the operator is prompted to enter the new value. In the present design fluid flow through path 10 is automatically and quickly stopped whenever an operator requests a selection menu. Operation resumes under control of any new parameters upon completion of any operator selections. However, it would be feasible to continue system operation during operator selections (after the initial start-up procedure) and adjust system operation to any operator selections as they are made.

The adaptive maximum flow rate value may also be automatically adjusted during system operation. If pressure sensor P1 24 suggests that an occlusion has occurred, fluid flow in path 10 is rapidly stopped and the adaptive maximum flow rate value is reduced by a predetermined value such as 40 ml/minute. If the occlusion is minor (such as illustrated graphically in FIG. 10) sensed pressure will begin to rise and normal operation will resume with the lower adaptive maximum flow rate value controlling the flow rate limit.

It should be appreciated that the adaptive maximum flow rate value is an upper limit which is superimposed upon flow rate commands that are determined using the control curves as discussed in conjunction with FIGS. 2 and 12. If the determined flow rate is below the adaptive maximum flow rate value, then the adaptive maximum flow rate value has no effect upon system operation, but is retained to limit the transient extraction rate following a start-up (such as the start of a new extraction subcycle or the recovery after an alarm situation).

Upon entry of the procedure-specific information, the system pauses and invites the operator to install the pressure cuff. Upon installation of the pressure cuff the system proceeds with prompts for venepuncture and connection of the blood and AC tubing to the phlebotomy needle 12. The operator then actuates the ADVANCE key and the system proceeds to a blood prime operation step.

During blood priming the system proceeds to prime at 25 ml per minute while sensing pressure to derive test point 2 data. The system 100 operates to prime the concentrated cell path through bubble detector 18, blood pump 26, and cell clamp 40 to concentrated cell container 42 until the fluid level in concentrated cell container 42 reaches the bottom sensor 114a. When blood is detected in the reinfusion reservoir, the system stops and senses the intravenous pressure at a 0 flow rate to establish test point 1 data. Blood clamp 32 is closed at this time. After the initial prime and following each reinfusion cycle a full prime is not required and a predetermined amount of blood of approximately 10 cc is pumped to clear the blood line between phlebotomy needle 12 and branch point 30 of concentrated cells so that they are not pumped to the separator 48.

Then cell clamp 40 closes, blood clamp 32 opens and the blood prime continues for the separator line with blood pump 26 pumping blood through bubble detector 18, pump 26, branch point 30, blood clamp 32, branch point 34, and branch point 46 to plasma separator 48. While the blood pump 26 is running, cell pump 64 operates at substantially the same speed to extract the fluid from plasma separator 48 and pump it into concentrated cell container 116 while the fluid is replaced by blood. During the initial prime the replaced fluid is primarily saline solution from the saline prime. After each reinfusion subcycle the fluid is primarily blood. If a rotating filter is used, the filter is accelerated to normal speed during this time. Priming continues until the concentrated cell container reaches the next to bottom indicator 114b.

As soon as concentrated cell container 42 is filled with priming fluids to the next to bottom indicator 114b the plasma clamp 52 is opened to begin the plasma separation operation and blood pump 26 is energized to produce the optimum flow rate as discussed in conjunction with FIG. 2. During the extraction cycle plasma separator 48 separates plasma from the whole blood with the plasma passing through hemoglobin detector 50 and plasma clamp 52 to plasma container 54. The remaining high density concentrated cell fluid passes from plasma separator 48 through cell pump 64 to concentrated cell container 42 under control of the cell pump 64. The plasma side of plasma separator 48 is maintained at atmospheric pressure because the plasma flows into a soft walled plasma container 54 which is subjected to atmospheric pressure. The pressure sensor 44 coupled to the inlet of plasma separator 48 through branch point 34 and branch point 46 thus indicates the transmembrane pressure for the separator filter membrane 49 within plasma separator 48.

During execution of the extraction cycle processor 102 operates to update system 100 status parameters every 50 msec. These status parameters include pressure sensor values, motor rotational counts, clamp status, fluid level indications, and status of the bubble detector 18 and operator panel 114. So long as neither the concentrated cell container 42 is indicated as being full by the concentrated cell level detector 114 nor the plasma container is indicated as being full by weight scale 58 the extraction cycle continues.

Initially, the system 100 uses a predetermined default value for flow constants defining the ratio of flow volume to rotational count for the blood pump 26 and cell pump 64. However, to achieve improved accuracy these flow constants are updated using actual volume data during each extraction-reinfusion cycle. Rotational counts (12 per revolution) are maintained while the fluid level in concentrated cell container 42 rises from sensor 114b to 114c. The weight of plasma container 54 is also stored for these points so that the corresponding volume change can be added to the known volume change in concentrated cell container 42 to get the total volume flow through blood pump 26. The extraction direction flow constant is similarly determined for blood pump 26 during each extraction part cycle. The new flow constants are then substituted for the old ones just before the blood line is primed for the second and each subsequent cycle.

When one of the fluid containers is detected as full, the system proceeds to execute a reinfusion cycle during which concentrated cells within concentrated cell container 116 are returned to the donor until the fluid level in concentrated cell container 42 reaches the bottom level indicator point 114a. After the concentrated cell container 42 is indicated as empty by concentrated cell level detector 114, the status of the plasma container 54 is tested. If it is not full the system measures P1 for the next cycle test point 1 data and the blood line is reprimed with blood, obtaining test point 2 data, and the next extraction cycle is executed as before.

If, following a reinfusion cycle the plasma container 54 is found to be full, the blood and concentrated cell fluid flow paths are flushed with saline as the blood and concentrated cell fluids flushed from the flow paths are returned to the donor subject in a reinfusion operation. Typically, the final reinfusion of saline solution continues until a selected quantity of saline solution sufficient to flush the plasma separator 48 and flow path from plasma separator 48 through concentrated cell container 42 and blood pump 26 has been flushed with saline solution. Then, cell clamp 40 is closed, separator clamp 32 is opened and flushing of saline solution from container 62 continues through branch point 46, branch point 34 and branch point 30 to the needle 12 under control of blood pump 26. Pumping of saline solution typically continues until a quantity of saline solution requested by the operator earlier in the procedure is infused into the subject. The system 100 then pauses for removal of the used disposables, and installation of new disposable apparatus pending activation of the advance key to begin a new plasmapheresis operation with a new subject.

Figure 5:
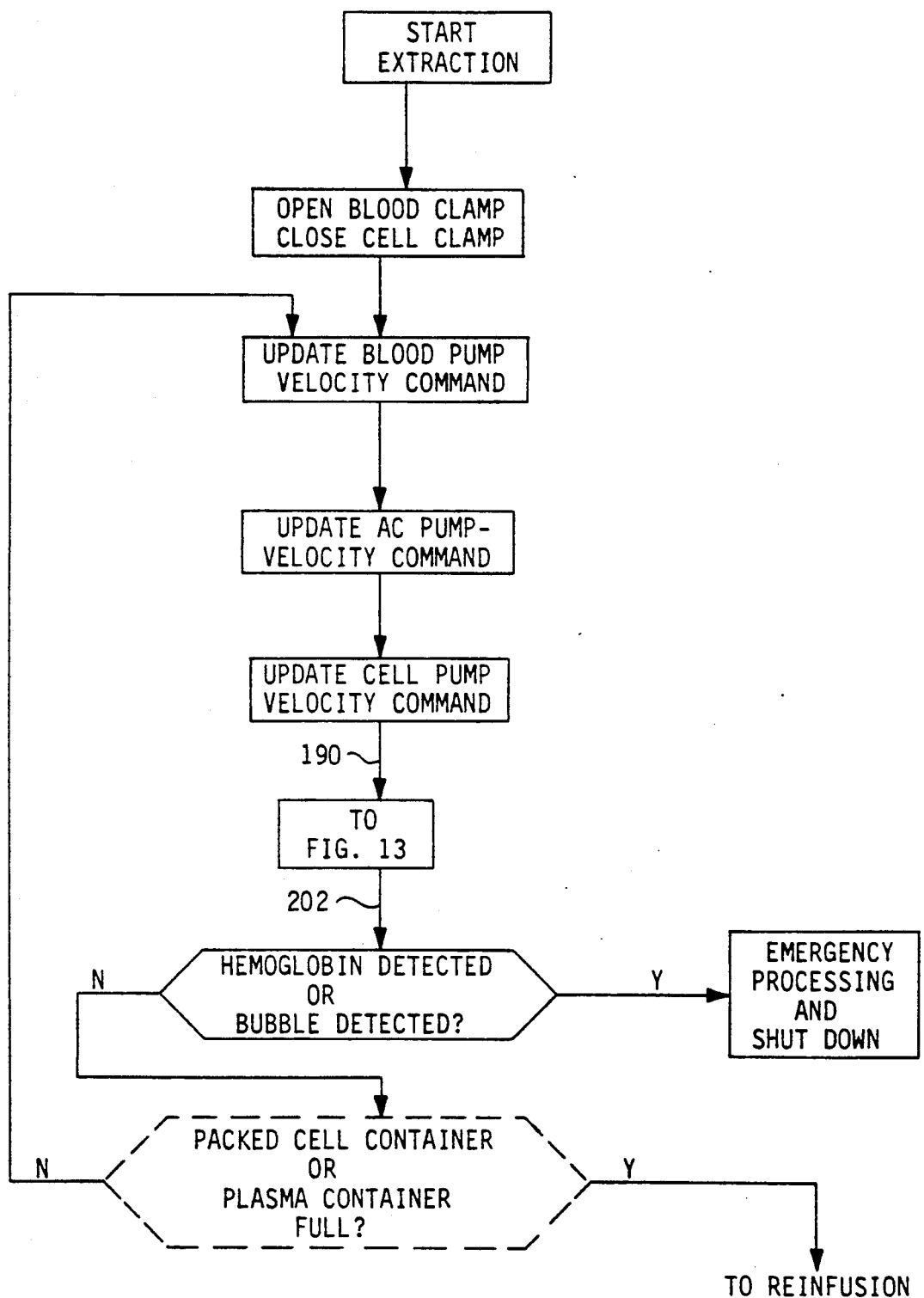
FIG. 5 is a flow chart illustrating in greater detail an extraction step used in the operation illustrated in FIG. 4.

A flow chart illustrating the execute extraction step shown in FIG. 4 is illustrated in greater detail in FIG. 5, to which reference is now made. Preliminarily the blood clamp is opened and the cell clamp is closed. The 50 msec extraction update computer cycle begins with an updating of blood pump and velocity commands as well as other commands for system operation not directly related to the blood flow control. This update computer cycle includes the acquisition of system status data and calculation of new command parameters. Also directly related to the blood flow control during extraction is the updating of the anticoagulant pump velocity command and the updating of the cell pump velocity command. At this point processor 102 executes the adaptive flow rate limit calculations indicated in FIG. 13 and described below. Upon return, processor 102 then looks at the acquired data from hemoglobin detector 50 and bubble detector 18. If either hemoglobin or a bubble are detected or any of the status parameters such as pressure are outside an acceptable range an emergency message is displayed and the system is shut down as part of an emergency processing operation.

Normally the hemoglobin and bubble tests will be negative and the processor 102 will test to see if either the packed cell level detector 114 indicates a full condition or the weight scale 58 indicates a full condition for the plasma container 54. If either container is indicated as being full the flow chart branches to a reinfusion cycle. Otherwise, the extraction update cycle is reexecuted.

Figure 6:
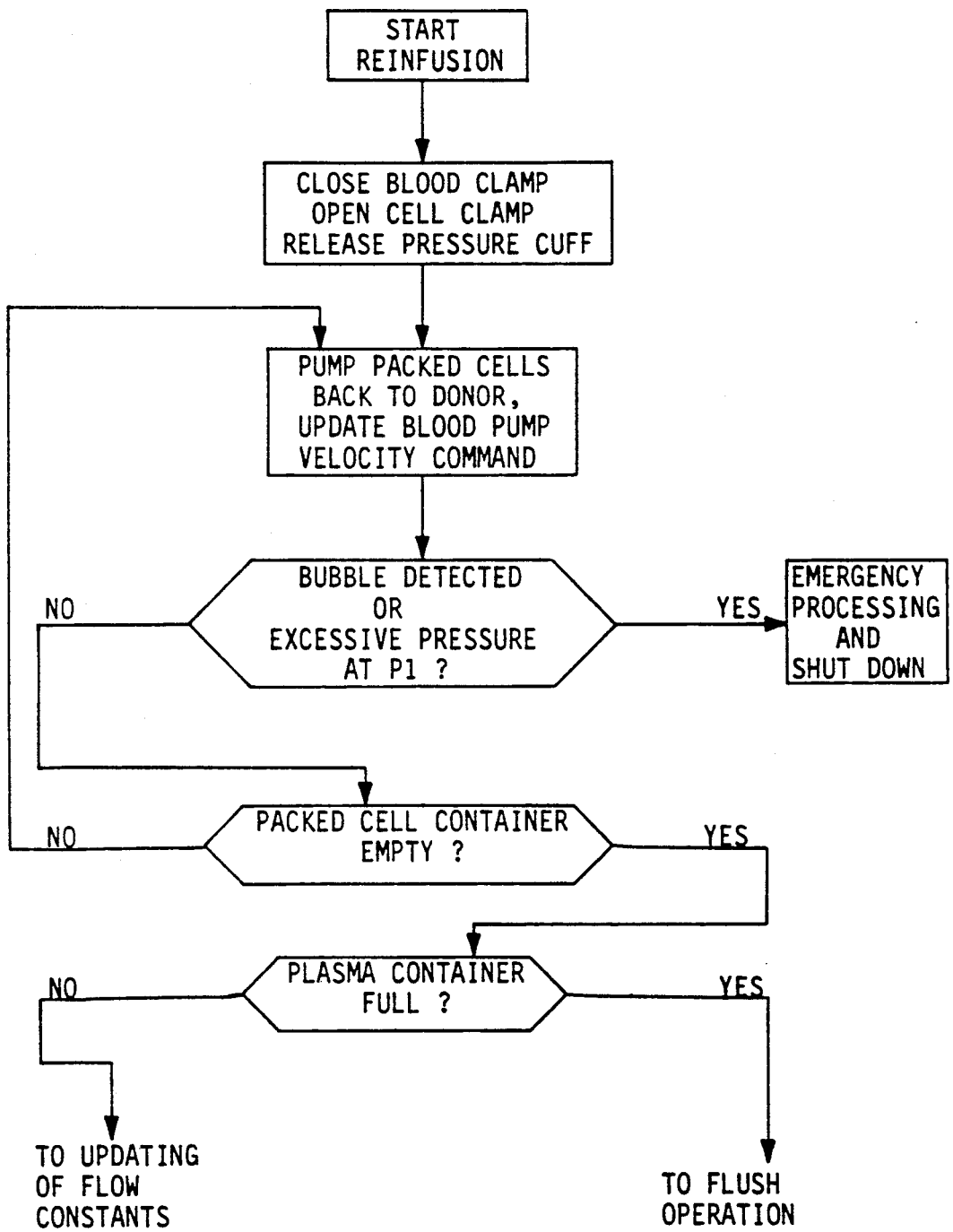
FIG. 6 is a flow chart illustrating in greater detail a reinfusion step used in the operation illustrated in FIG. 4.

The reinfusion cycle of FIG. 4 is illustrated in greater detail in the flow chart of FIG. 6 to which reference is now made. At the start of reinfusion the blood clamp 20 is closed, cell clamp 40 is opened and cuff clamp 112 is open to release pressure in the pressure cuff. The system then proceeds to pump packed cells back to the donor subject, with the blood pump velocity command being updated on a 50 msec cycle as was the case during extraction. However, during reinfusion the translated reinfusion flow rate limit curve 94 is utilized as shown in FIG. 2 rather than the extraction flow rate limit curve 78 which is used for extraction.

During reinfusion a test is then made for sensing of bubbles by bubble detector 18 and excessive pressure at P1. The sensing of pressure by P1 pressure sensor 24 at this point is an extra limit test over and above the normal flow rate update which occurs in conjunction with the flow rate calculation of flow rate control parameters. If a bubble is detected or the pressure at P1 is above the predetermined limit, emergency processing begins with the display of an emergency message and the system 100 is shut down with all pumps being rapidly stopped. Normally the system will detect that neither a bubble nor excessive pressure exists, and it will then test the level indication data from concentrated cell level detector 114. If concentrated cell container 42 is not empty, the cycle repeats. However, if the concentrated cell container is indicated as being empty, a test is made as to whether or not the plasma container is full. If the plasma container is full the operation of system 100 proceeds to flush the disposables as indicated in FIG. 4. If plasma container 54 is not full, then the system proceeds to a new extraction cycle after updating the pump flow constants and reinflating the pressure cuff.

Figure 7:
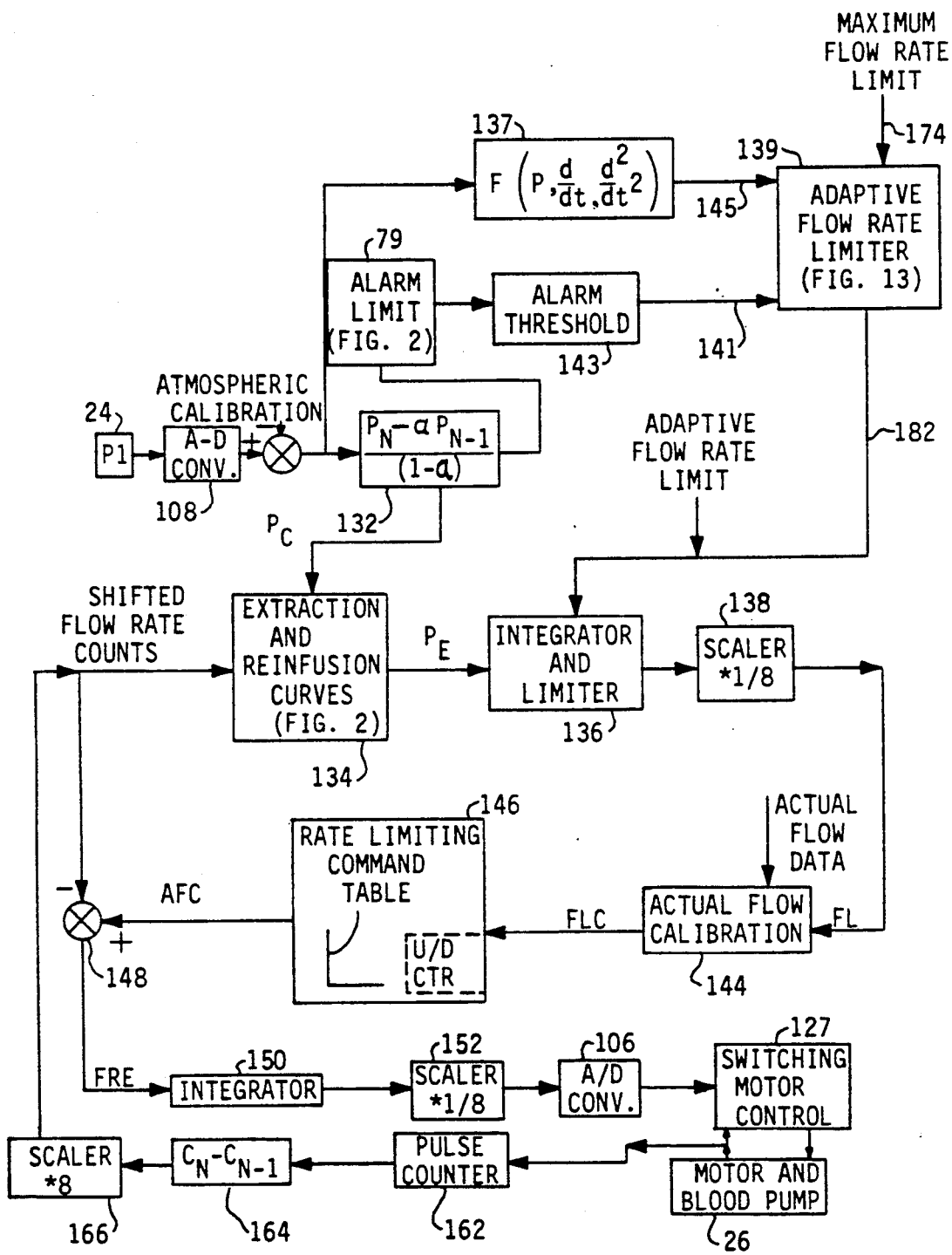
FIG. 7 is a functional block diagram representation of a flow rate control update cycle for the adaptive flow rate control system.

An adaptive flow rate control system 130 controlling the operation of a motor M2 driving blood pump 26 is illustrated in functional block diagram form in FIG. 7, to which reference is now made. While not shown explicitly, it will be appreciated that the digital mathematical operations are executed by processor 102 (FIG. 3). In general, the adaptive control system 130 responds to pressure indications from P1 pressure sensor 24 and actual motor velocity count signals from motor M2 for blood pump 26 to generate motor velocity command signals for motor M2 and blood pump 26.

The operation of motor M1 driving AC pump 114 and motor M3 driving cell pump 40 are scaled relative to motor M2 driving blood pump 26. For example, AC pump 14 might pump 1 to 5 percent of the volume of blood pump 26 while cell pump 40 pumps 50% of the volume of blood pump 26. Except for the velocity scaling, the velocity control systems for the motors driving AC pump 111 and cell pump 40 are essentially the same as system 130 and are therefore not separately shown.

Pressure indications received from P1 pressure sensor 24 are converted to digital form by analog-to-digital converter 108 and communicated to processor 102. The digital pressure values are calibrated to place a zero pressure indication at atmospheric pressure by subtracting an atmospheric calibration factor. The calibrated pressure is then subjected to a lead lag compensation function in the form $$P_c = [P_n - \alpha P_{n-1}]/[1 - \alpha].$$

where $P_n$ is the current calibrated pressure indication, P is the lead lag compensated pressure indication from the preceding update cycle, and $P_C$ is the resulting compensated pressure indication. It will be recalled that during operation of blood pump 26 the motor M2 velocity command is updated repetitively on a 50 msec cycle. $\alpha$ is a proportioning constant which might typically be about 0.5. The lead lag compensation of the calibrated pressure indication is represented by a block 132 and tends to compensate for ramping delays and other delays at other parts of the control system to improve stability of system operation.

The compensated pressure indication, $P_c$, is communicated to a step 134 at which the appropriate extraction or reinfusion flow rate limit curve from FIG. 2 is applied to system status parameters to generate a pressure error signal $P_E$. At step 134 a shifted or scaled flow rate count signal which represents actual velocity for blood pump 26 is mathematically applied to the equation representing the appropriate flow rate limit curve to generate the pressure at which the flow rate limit curve intersects the actual system flow rate to generate a limit pressure $P_L$. A pressure error signal, $P_E$ is then generated as the difference between $P_C$ and $P_L$ with the sign of $P_E$ being positive if the actual pressure $P_C$ is within the limit point and negative if $P_C$ is beyond the limit point. In other words, for extraction $P_E = P_C - P_L$ and for reinfusion $P_E = P_L - P_C$ where $P_C$ and $P_L$ are signed real numbers. The net result, is a value for $P_E$ which increases negatively as flow rate increases beyond the point at which sensed pressure magnitude is outside the bounds of the flow rate limit curve during either extraction or reinfusion. It is noted that the motor M2 direction of rotation is independently controlled by processor 102 with only the speed of rotation being controlled by the adaptive flow rate control system 130.

At an integrator and limiter step 136 the pressure error value $P_E$ is integrated to help assure that any flow rate errors are corrected to zero, or within some threshold level of acceptable deviation. The integrated values are then limited to a selected maximum positive value corresponding to the adaptive maximum flow rate value, which is determined and stored as previously described. Any negative value for the integrated pressure error signal (indicating that actual flow rate is beyond the acceptable limits) is limited to zero to avoid any improper response by the directionless speed magnitude control system.

Differentiator 137, which can also be a matched filter, also operates to receive the pressure error value $P_E$ and to generate an output signal $F(P,(S,S^2)P)$. The signal $F(P,(S,S^2)P)$ represents a function of the first and second derivatives of pressure with respect to time and is useful to provide an early identification of a transient path 138 crossing substantially below the translated flow rate limit curve 77 of FIG. 11.

Differentiator 137 provides a vehicle for quick response to pressure conditions indicative of the onset of an occlusion. Experience has indicated that first order regulation of the control system is inadequate to avoid occlusions in some instances as discussed above in reference to FIGS. 8–12. Other elements for accelerating the system response to the onset of an occlusion, described more fully below, include the use of graduated decrements, graduated slew rate limiting and reverse pump action. These elements facilitate increased efficiency and dynamic range of the blood extraction system, while decreasing the occlusion rate.

The output from the differentiator 137 is communicated to adaptive flow rate limiter 139 which processes information from the maximum flow rate limit, alarm threshold output 14, and differentiator 137.

The adaptive flow rate limiter 139 (FIG. 13) establishes the adaptive flow rate limit 182 that is impressed on the output of the integrator in 136 to limit blood rate in order to limit the rate of depletion of the blood in the region of the needle following a start-up of the blood pump.

In accordance with the present invention, and as discussed more fully herein below, the following variables are defined as set forth in Table I.

TABLE I

| | |
|---|---|
| BLDFLO = | CURRENT ACTUAL PUMP FLOW RATE (ml/minute) |
| BOFFSET = | FLOW RATE LIMIT MARGIN (ml/minute) |
| EXTRATE = | CURRENT ADAPTIVE FLOW RATE LIMIT (ml/minute) |
| MAXEXTRATE = | MAXIMUM FLOW RATE LIMIT (ml/minute) |
| HIGHCOUNTER = | A REGISTER THAT IS INCREMENTED WHEN BLDFLO MOVES ABOVE A PRESET MAXIMUM BLOOD FLOW |
| LOWCOUNTER = | A REGISTER THAT IS INCREMENTED WHEN BLDFLO FALLS BELOW A PRESET MINIMUM BLOOD FLOW |
| HIGHTIME = | THE COUNT ASSOCIATED WITH HIGHCOUNTER WHEN THE VALUE OF EXTRATE IS TO BE RAISED |
| LOWTIME = | THE COUNT ASSOCIATED WITH LOWCOUNTER WHEN THE VALUE OF EXTRATE IS TO BE LOWERED |

Figure 13:
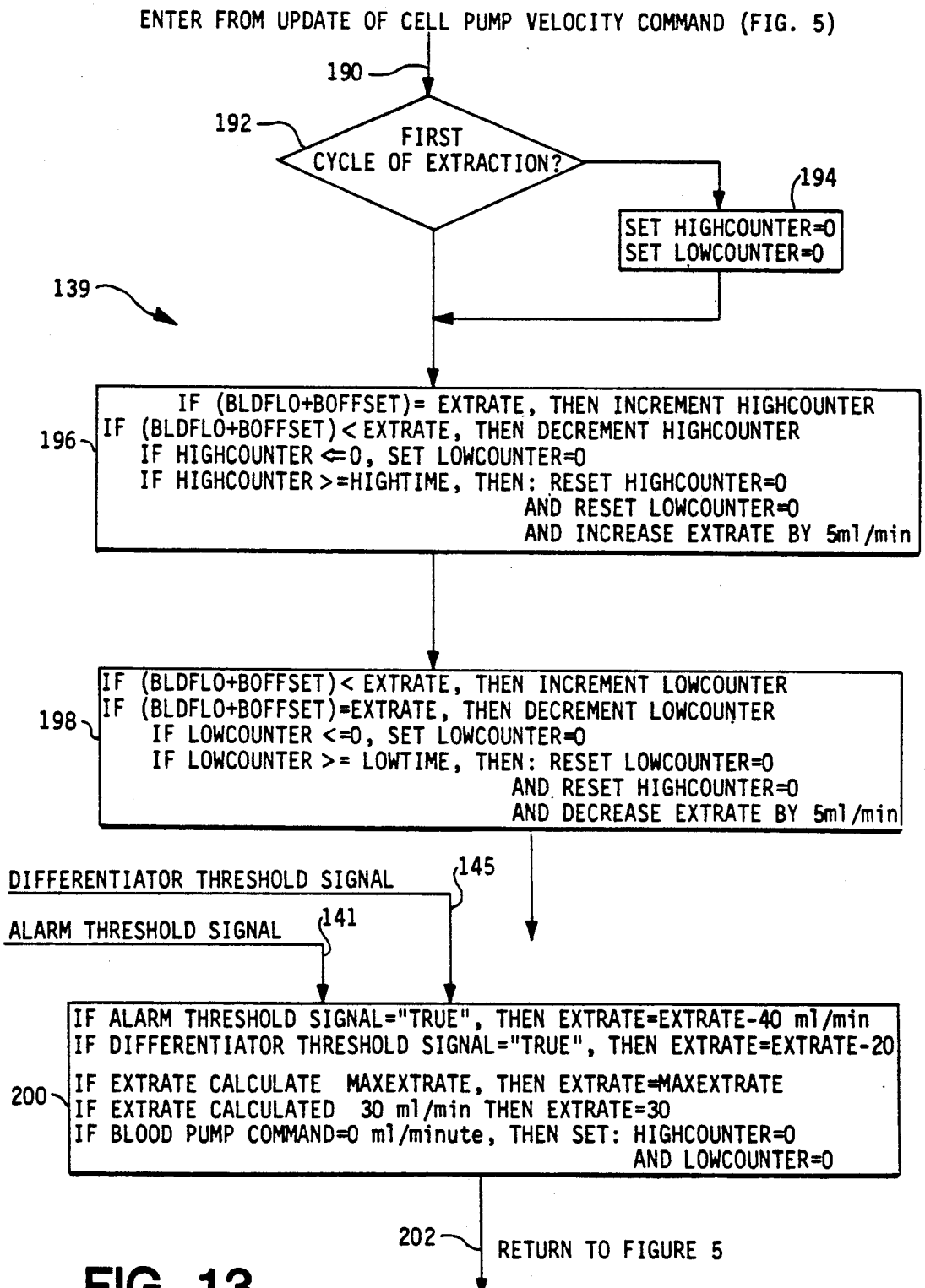
FIG. 13 is a flow chart illustrating an adaptive flow rate limiter.

With reference to FIG. 13, the processor calculates and/or otherwise defines values for each of the variables set forth in TABLE I for the purpose of making adjustments to the "adaptive flow rate limit", hereinafter referred to by the acronym EXTRATE. HIGHCOUNTER is a register that counts consecutive occurrences of 50 millisecond computer cycles in which the controlled blood pump in response to the control system approaches close to the adaptive flow rate limit EXTRATE. HIGHTIME is an accumulated time after which it is desirable to raise EXTRATE (for example 15 seconds). Similar definitions for lowering EXTRATE apply to LOWCOUNTER and LOWTIME (for example 18 seconds).

Each computer cycle of 50 milliseconds during the extraction subcycle the flow diagram of FIG. 13 is executed. A check is made in 192 to determine if the extraction subcycle is just starting wherein HIGHCOUNTER and LOWCOUNTER are set to zero in 194.

Block 196 examines the current blood pump rate and determines if it is within BOFFSET (for example 5 ml/minute) of EXTRATE. That is, if it is within a target flow range zone 183 between EXTRATE and (EXTRATE −5 ml/min). If at EXTRATE, it increments HIGHCOUNTER. If below EXTRATE, it decrements HIGHCOUNTER. A test is made to determine if HIGHCOUNTER has reached HIGHTIME, and if so, then EXTRATE is increased by 5 ml/minute.

Similar logic is performed in block 198 to decrease EXTRATE if the controlled blood pump is consistently below (EXTRATE −5) ml/minute.

In this way EXTRATE is made to follow the controlled blood pump rate so that, in response to a start-up, the transient path will be controlled and avoid occlusions.

Step 200 provides limit testing to insure that EXTRATE remains within bounds, and provides that the counters are reset to zero during occlusions and other times when the blood pump is commanded to zero flow rate.

As shown in FIG. 7, the output signal is communicated to scaler 138 which is operative to scale the combined signal by ⅛ to insure scale compatibility with other system parameters.

The limited flow command, designated FL, is applied to an actual flow calibration step 144 during which the flow constant is utilized to calibrate the limited flow command, FL to produce a calibrated flow command signal FLC. As explained previously, a predetermined value is used for the first extraction-reinfusion cycle with the value being determined from actual data during subsequent cycles. The noninvasive peristaltic pumps which are utilized to force fluid through the fluid flow path in plasmapheresis system 100 comprise four equally spaced rollers which squeeze flexible tubing defining the flow path between the rollers and a circular peripheral wall. The amount of fluid which is actually pumped during a quarter turn of the pump head depends on how much fluid is within the flow path between two adjacent rollers rotating against the peripheral wall. This quantity of fluid in turn depends upon the exact inside diameter of the flow path tubing and since the tubing must inherently be somewhat flexible and resilient, depends also upon the pressure of the fluid and the exact elasticity of the tubing. Since different sets of disposable tubing are utilized for each plasmapheresis operation and since system pressures are not always identical for different plasmapheresis operations, small but significant variations occur in the relationship between the velocity of blood pump 26 which is sensed by the adaptive flow rate control system 130 and the actual fluid flow rate.

By calibrating the limited flow command, FL, during extraction, the volume of plasma which is removed from the blood of the subject donor by plasma separator 48 can be optimized.

The calibrated FL signal is applied to an acceleration limiting command table step 146. The acceleration limiting command table includes a 256 word by 8 bit lookup table and an indexing or counting register which stores an address for accessing the lookup table.

The counter register is controlled to be incremented or decremented one count at a time in response to the calibrated flow command signal FLC. If FLC is greater than the counter value, the counter is incremented by one. If FLC is less than the counter value, the counter is decremented by one. The counter value is then used to access the lookup table to produce a table value. Then an adjusted flow control signal, AFC, is updated using either the table value of signal FLC, or FLC itself, whichever results in the smallest change in magnitude of signal AFC from the current magnitude determined from the previous update cycle.

For larger flow values the table value can change by several units for each increment in the counter value. By using the smaller change produced by FLC or the table value, signal AFC can stabilize under steady state conditions at values intermediate the table values to provide more precise velocity control.

The table of values for acceleration limiting command table 146 is exponential in nature. The table produces values of 0, 9, 10, for inputs of 0, 1, 2 and 3 respectively. The zero assures that zero input produces a zero output while the jump to 9 at the next step compensates for offsets in the particular D-A converter 106. Each step in the table increments by 1.03 over the previous step. For small input address values this step rounds to one. For larger values around 100 the step accordingly becomes 3.

The exponential relationship built into the table enables it to be used to control all three pumps 14, 26, 40 and hence reduce memory requirements. If the table were linear, AC pump 14 and cell pump 40 would accelerate proportionately more rapidly than blood pump 26. For example, full speed for blood pump 26 might correspond to FLC=90 and would require 90 update cycles for blood pump 26 to accelerate to full speed. The slower AC pump 14 and cell pump 40 might require FLC=30 or 40 and thus reach full speed in 30 or 40 update cycles. These pumps would then be running proportionately fast during the remaining 60 or 50 counts required for blood pump 26 to accelerate to full speed. The exponential table relationship enables speed changes in all three pumps 14, 26 and 40 to remain approximately in proportion while using a single lookup table for all of them.

At a subtraction step 148 the shifted flow rate count cycle for the latest 50 msec update interval is subtracted from the newly calculated adjusted flow rate command signal to generate a flow rate error signal, FRE, equal to the difference between the adjusted flow rate command signal and the actual flow rate. The flow rate error signal is integrated at an integrator step 150 and scaled by multiplication by ⅛ at a scaler step 152 prior to presentation to the digital-to-analog converter 106 (see FIG. 3). Digital-to-analog converter 106 converts the integrated and scaled flow rate error signal to an analog flow rate error signal which is applied to a PWM motor control circuit 160. PWM motor control circuit 160 includes a wide bandwidth PWM motor drive circuit of conventional nature and in effect represents a wide bandwidth servo loop within a narrower bandwidth digital servo loop.

Blood pump motor M2 has attached thereto a Hall effect sensor arrangement which produces 12 output pulses for each 360° of rotation of motor M2. These pulses are detected and counted at a pulse counter step 162. The pulse count outputs are applied to a subtractor step 164 and a multiply by 8 scaler step 166 to generate the shifted flow rate counts which are applied to the extraction and reinfusion curves 134 and the subtractor 148. Pulse counter 162 produces an output which represents motor rotational position. Subtractor 164 in effect operates as a differentiator to convert the position signal to a velocity signal by subtracting a previous count from a current count to produce a count difference corresponding to velocity. This difference is scaled by scaler 166 to generate the shifted flow rate counts signal.

The adaptive flow rate control system 130 thus operates on 50 msec repetitive updata computer cycles (sample rate) during extraction or reinfusion to control the velocity of motor M2 which drives blood pump 26 to assure that bodily fluid flow either to or from the subject occurs at the maximum possible rate without exceeding the accommodation capability of the donor subject or the 150 ml per minute design limit of the system. This optimiziation of the bodily fluid flow rate assures optimum utilization of the equipment and minimum inconvenience and discomfort to the subject while precluding vein collapses which might occlude the needle during extraction or excessive pressure during reinfusion.

During normal stoppage of pumps 14, 26 and 40, the normal control algorithm shown in FIG. 7 is partially bypassed with the output of integrator and limiter 136, the output of integrator 150 and the index counter for acceleration limiting command and table 146 all being set directly to zero in each of the control algorithms for the three pumps. If an emergency shutdown is executed, as when a negative value of 20 or more for the output of integrator and limiter 136 indicates that the actual operating point is far outside the appropriate flow rate limit curve, or as when differentiator 137 detects the onset of an occlusion, the blood pump motor is merely given a reverse direction command until an update cycle produces a shifted flow rate counts signal of substantially zero. This suggests a very low or zero velocity. Then the normal stop procedure is executed as described above.

Whenever the integrator and limiter 136 outputs an error value of 20 or more during an extraction cycle the occurrence of an occlusion is suggested. In order to reduce the probability of additional occlusions occurring as soon as the system returns to full speed, the adaptive current maximum flow rate value (EXTRATE) is reduced by 40 ml per min. If a subject cannot supply blood at the minimum threshold value it is presumed that either the needle 12 is not properly inserted or else that the subject is not a suitable candidate for use.

The adaptive flow rate control system 130 thus operates to maintain bodily fluid flow rate as high as possible without exceeding the accommodation capability of the subject or the 150 ml per minute design flow rate of the plasmapheresis system 100. The control system 130 thus assures maximum utilization of the equipment and minimum inconvenience and discomfort to the donor subject while protecting against occlusion of the needle 12 because of vein collapse or tissue damage from excessive intravenous pressure.

While there has been shown and described above as adaptive flow rate control system which is particularly useful for controlling bodily fluid flow rates in a plasmapheresis system for the purpose of enabling a person of ordinary skill in the art to make and use the invention, it will be appreciated that the invention is not limited thereto. Accordingly any modifications, variations or equivalent arrangements within the scope of the attached claims should be considered to be within the scope of the invention.

What is claimed is:

1. A system for controlled withdrawal of blood from a blood vessel, said system comprising:

a fluid reservoir fluidly connected to said blood vessel by a first fluid flow path;

a pump for pumping blood from said blood vessel through said first fluid flow path to said fluid reservoir;

a pressure sensor for sensing the pressure within said first fluid flow path;

a flow rate sensor for sensing the flow rate within said first fluid flow path;

an adaptive flow rate control system operatively connected to (1) said pressure sensor, (2) said flow rate sensor and (3) said pump, to receive pressure and flow rate signals from said pressure and flow rate sensors and to send control signals to said pump;

said adaptive flow rate control system comprising:
   (a) means for receiving and storing a maximum flow rate limit setting entered by an operator;
   (b) means for receiving said pressure and flow rate signals from said pressure sensor and said flow rate sensor and for generating therefrom and storing a standard flow rate/pressure curve defining the flow rate/pressure relationship of blood passing freely through said blood vessel and said first flow path without substantially reduced pressure within said blood vessel as determined;
   (c) means for calculating a control curve in relation to, and below, said standard flow rate/pressure curve;
   (d) means for setting an initial adaptive flow rate limit no greater than said maximum flow rate setting;
   (e) means for signaling said pump to pump blood at a rate substantially equal to said initial adaptive flow rate, for a first timed pumping period;
   (f) means for sensing whether the pressure within the first flow path has remained above the control curve throughout the immediately preceding timed pumping period and, if so, for increasing the adaptive flow rate limit by a predetermined increment amount and, thereafter, for signaling the pump to pump blood at the increased adaptive flow rate limit, for a subsequent timed pumping period;
   (g) means for sensing whether the pressure within the first flow path has fallen below the control curve and, if so, for signaling the pump to decrease the flow rate to a rate at which steady-state pressure on said control curve is established for a timed stabilization period;

(h) means for determining, after completion of the timed stabilization period, whether the point on said control curve whereat steady-state pressure has been established for said stabilization time period is more than a predetermined amount below said adaptive flow rate limit, and if so, for:

decreasing the adaptive flow rate limit by a predetermined decrement amount to establish a decreased adaptive flow rate limit and, thereafter;

signaling the pump to pump at said decreased adaptive flow rate limit for a subsequent timed pumped period.

2. The system of claim 1 wherein the predetermined amount below said adaptive flow rate limit is 2 to 20 ml/min.

3. The system of claim 1 wherein the predetermined amount below said adaptive flow rate limit is 4 to 6 ml/min.

4. The system of claim 2 wherein said increment amount is between about 2 and 20 ml/min.

5. The system of claim 2 wherein said decrement amount is between about 2 and 20 ml/min.

6. The system of claim 2 wherein said increment amount is approximately 5 ml/min.

7. The system of claim 2 wherein said decrement amount is approximately 5 ml/min.

8. The system of claim 2 wherein said decrement amount is approximately 10 ml/min.

9. The system of claim 1 wherein each timed pumping period is approximately 10 to 60 seconds in length.

10. The system of claim 2 wherein each timed pumping period is approximately 15 seconds in length.

11. The system of claim 2 wherein the initial maximum flow rate limit is 150 ml/min.

12. The system of claim 2 wherein said initial adaptive flow rate limit is 120 ml/min.

13. The system of claim 12 wherein said control system further comprises:

means for calculating and monitoring the rate of change of pressure with respect to time;

means for determining when the rate of change of pressure with respect to time is indicative of progressing occlusion of said flow path; and in response thereto, means for signaling said pump to correctively decrease the flow rate through said first flow path so as to avert full occlusion of said flow path.

14. The system of claim 13 wherein said control system is programmed to calculate and monitor the rate of change of pressure with respect to time by calculating at least one derivative function of pressure.

15. The system of claim 14 wherein the control system is programmed to calculate and monitor the first derivative dp/dt of pressure.

16. The system of claim 14 wherein the control system is programmed to calculate and monitor pressure, and the first derivative dp/dt and the second derivative $dp^2/dt^2$ of pressure.

17. The system of claim 16 wherein said control system further comprises means for generating at least one signal of at least one derivative function of pressure and to combine said signal of at least one derivative function of pressure with said pressure signal to produce a composite signal from which an indication of occlusion of said fluid flow path may be discerned.

18. The system of claim 1 wherein said timed stabilization period is approximately 10–60 seconds in length.

19. The system of claim 1 wherein said timed stabilization pumping period is about 18 seconds in length.

20. The system of claim 2 further adapted for controlled infusion of fluid into a blood vessel, through a return fluid flow path fluidly connecting said system to a blood vessel wherein said control system further comprises:

means for changing the sign of said control curve so as to establish a base infusion control curve which directly corresponds to said control curve;

means for raising said base infusion control curve by a predetermined pressure adjustment factor;

means for altering the slope of said infusion control curve by a predetermined slope adjustment factor.

21. The system of claim 20 wherein said control system is specifically programmed and to apply a predetermined pressure adjustment factor of approximately 48 mm Hg.

22. The system of claim 20 wherein said control system is specifically programmed to apply a slope adjustment factor of approximately −2.0.

23. The system of claim 2 further comprising:

at least one mathematical signal conditioner connected to said pressure sensor to condition said pressure signal to optimize the usability of said pressure signal as an indicator of blood vessel occlusion.

24. The system of claim 23 wherein said mathematical signal conditioner comprises a plurality of correlation filters.

25. The system of claim 23 wherein said mathematical signal conditioner comprises a plurality of matched filters.

26. The system of claim 25 wherein said matched filters are matched to a typical pressure signal and mismatched to typical noise.

27. The system of claim 23 wherein said mathematical signal conditioner comprises a means for analyzing said pressure signal by convolution matched filter functions.

28. An extracorporeal blood processing system wherein blood is withdrawn from a blood vessel through a first flow path, processed in an extracorporeal processing apparatus and at least a portion of the blood is then infused from said blood processing apparatus through a second flow path into a blood vessel, said system comprising:

a blood processing apparatus for effecting a desired processing of blood;

a first flow path fluidly connectable between a blood vessel and said blood processing apparatus to permit withdrawal of blood from said blood vessel into said blood processing apparatus;

a second flow path fluidly connectable between said blood processing apparatus and a blood vessel for infusing at least a portion of said blood from said blood processing apparatus into a blood vessel;

a withdrawal pump operatively mounted to said first flow path to pump blood from said blood vessel to said blood processing means;

an infusion pump operatively mounted to said second flow path to pump blood from said blood processing means to said blood vessel;

a first pressure sensor for sensing pressure within said first flow path;

a first flow rate sensor for sensing flow rate within said first flow path;

a second pressure sensor for sensing pressure within said second flow path;

a second flow rate sensor for sensing flow rate within said second flow path;

a flow rate control system operatively connected to (1) said first and second pressure sensors; (2) said first and second flow rate sensors; and (3) said withdrawal and infusion pumps to receive pressure and flow rate signals from said first and second pressure sensors and said first and second flow rate sensors and to send control signals to said pump(s); said flow rate control system comprising:

(a) means for receiving and storing a maximum withdrawal flow rate limit setting entered by the operator;

(b) means for receiving and storing a maximum infusion flow rate limit set by the operator;

(c) means for utilizing pressure and flow rate signals from said first flow path to generate a standard withdrawal flow rate/pressure curve defining the flow rate/pressure relationship of blood being withdrawn through said first flow path;

(d) means for calculating a withdrawal control curve in relation to, and below, said standard withdrawal flow rate/pressure curve;

(e) means for changing the sign of said withdrawal control curve to establish a base infusion control curve;

(f) means for raising said base reinfusion control curve by a predetermined adjustment factor to establish an upwardly adjusted infusion control curve prior to beginning infusion through said second flow path;

(g) means for altering the slope of said adjusted infusion control curve by a predetermined slope adjustment factor prior to beginning infusion through said second flow path.

29. The system of claim 28 wherein said blood processing apparatus comprises an apparatus for separating the blood into at least first and second constituent portions and wherein at least one of said constituent portion is infused from said blood processing apparatus through said second flow path.

30. The system of claim 29 wherein said blood processing apparatus is an apheresis apparatus.

31. The system of claim 30 wherein said apheresis apparatus comprises a plasmapheresis apparatus for separating and removing a portion of the plasma from the withdrawn blood.

32. The system of claim 30 wherein said apheresis apparatus comprises a plasmapheresis apparatus for separating and removing a portion of the plasma from the withdrawn blood.

33. The system of claim 28 wherein said blood processing apparatus comprises apparatus for effecting therapeutic plasma exchange wherein a quantity of autologous plasma is separated and removed from said blood and, thereafter, a quantity of diluent fluid is added to the plasma depleted blood and, thereafter, the admixture of said plasma depicted blood and said diluent fluid is reinfused through said second flow path.

34. The system of claim 28 wherein said flow rate control system further comprises:

(h) means for setting an initial adaptive withdrawal flow rate limit no greater than said maximum withdrawal flow rate setting entered by the operator;

p1 (i) means for signaling said withdrawal pump to withdraw blood at a rate substantially equal to said initial adaptive withdrawal flow rate for a first timed pumping period;

(j) means for sensing whether the pressure within said first flow path has remained above the withdrawal control curve throughout the immediately preceding timed pumping period and, if so, for increasing the adaptive withdrawal flow rate limit by a predetermined increment amount and, thereafter, for signaling the pump to pump blood at the increased adaptive withdrawal flow rate limit for a subsequent timed pumping period;

(k) means for sensing whether the pressure within the first flow path has fallen below the control curve and, if so, for signaling the pump to decrease the withdrawal flow rate to a rate at which steady-state pressure on said withdrawal control curve is established for a timed stabilization period.

35. The system of claim 34 wherein the flow rate control system further comprises:

(1) means for determining, after completion of the timed stabilization period, whether the point on said withdrawal control curve whereat steady-state pressure has been established for said stabilization time period is more than a predetermined amount below said adaptive flow rate limit, and if so, for:

decreasing the adaptive withdrawal flow rate limit by a predetermined decrement amount to establish a decreased adaptive withdrawal flow rate limit and, thereafter, signaling the pump to withdraw blood at said decreased adaptive withdrawal flow rate limit for a subsequent timed pumping period.

36. The system of claim 28 wherein said flow rate control system further comprises:

(h) means for setting an initial adaptive infusion flow rate limit no greater than said maximum infusion flow rate setting entered by the operator;

(i) means for signaling said infusion pump to infuse blood at a rate substantially equal to said initial adaptive infusion flow rate for a first timed pumping period;

(j) means for sensing whether the pressure within said second flow path has remained above the infusion control curve throughout the immediately preceding timed pumping period and, if so, for increasing the adaptive infusion flow rate limit by a predetermined increment amount and, thereafter, for signaling the pump to pump blood at the increased adaptive infusion flow rate limit for a subsequent timed pumping period;

(k) means for sensing whether the pressure within the second low path has fallen below the control curve and, if so, for signaling the pump to decrease the infusion flow rate to a rate at which steady-state pressure on said infusion control curve is established for a timed stabilization period.

37. The system of claim 36 wherein the flow rate control system further comprises:

(1) means for determining, after completion of the timed stabilization period, whether the point on said infusion control curve whereat steady-state pressure has been established for said stabilization time period is more than a predetermined amount below said adaptive flow rate limit, and if so, for:

decreasing the adaptive infusion flow rate limit by a predetermined decrement amount to establish a deceased adaptive infusion flow rate limit and, thereafter, signaling the pump to infuse blood at said decreased adaptive infusion flow rate limit for a subsequent timed pumping period.

38. The system of claim 28 wherein said means for raising said base reinfusion control curve by a predetermined adjustment factor comprise means for raising said withdrawal control curve by approximately 48 mm Hg.

39. The system of claim 28 wherein said means for altering the slope of said adjusted infusion control curve comprises means for multiplying the slope of said adjusted infusion control curve by a slope correction factor of approximately −2.0.

40. The system of claim 28 wherein said system is a two-needle apheresis system wherein said first flow path is connectable to a blood vessel by way of a first needle and said second flow path is connectable to a blood vessel by way of a second needle.

41. The system of claim 28 wherein said first flow path is fluidly connectable to a first blood vessel by way of a first needle and said second flow path is fluidly connectable to a second blood vessel by wa of a second needle.

42. The system of claim 28 further comprising:
at least one mathematical signal conditioner connected to said first pressure sensor to condition the pressure signal received from said first pressure sensor as to optimize the usability of said pressure signal received from said first pressure sensor as an indicator of blood vessel occlusion.

43. The system of claim 42 wherein said mathematical signal conditioner comprises a plurality of correlation filters.

44. The system of claim 42 wherein said mathematical signal conditioner comprises a plurality of matched filters.

45. The system of claim 44 wherein said matched filters are matched to typical withdrawal pressure signals and mismatched to typical noise.

46. The system of claim 42 wherein said mathematical signal conditioner comprises a means for analyzing the pressure signal received from said first pressure sensor by convolution matched filter functions.

47. The system of claim 28 further comprising:
at least one mathematical signal conditioner connected to said second pressure sensor to condition the pressure signal received from said second pressure sensor to optimize the usability of said pressure signal received from said second pressure sensor as an indicator of overpressurization during infusion.

48. The system of claim 47 wherein said mathematical signal conditioner comprises a plurality of correlation filters.

49. The system of claim 47 wherein said mathematical signal conditioner comprises a plurality of matched filters.

50. The system of claim 49 wherein said matched filters are matched to typical infusion pressure signals and mismatched to typical noise.

51. The system of claim 47 wherein said mathematical signal conditioner comprises a means for analyzing the pressure signal received from said second pressure sensor by convolution matched filter functions.

* * * * *